(12) United States Patent
McDermott et al.

(10) Patent No.: US 12,070,577 B2
(45) Date of Patent: Aug. 27, 2024

(54) SYSTEM AND METHOD FOR FLUID DELIVERY USING PRESSURE-BASED MOTOR CONTROL FOR FLUID INJECTOR DEVICES

(71) Applicant: BAYER HEALTHCARE LLC, Whippany, NJ (US)

(72) Inventors: Michael McDermott, Berlin (DE); William Barone, Pittsburgh, PA (US); Randy Lee, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 257 days.

(21) Appl. No.: 17/776,332

(22) PCT Filed: Nov. 20, 2020

(86) PCT No.: PCT/US2020/061474
§ 371 (c)(1),
(2) Date: May 12, 2022

(87) PCT Pub. No.: WO2021/102242
PCT Pub. Date: May 27, 2021

(65) Prior Publication Data
US 2022/0395633 A1    Dec. 15, 2022

Related U.S. Application Data

(60) Provisional application No. 62/938,397, filed on Nov. 21, 2019.

(51) Int. Cl.
*A61M 5/145* (2006.01)
*A61M 5/142* (2006.01)

(52) U.S. Cl.
CPC ............... *A61M 5/14566* (2013.01); *A61M 2005/14208* (2013.01); *A61M 2205/332* (2013.01);

(Continued)

(58) Field of Classification Search
CPC ............ A61M 5/14248; A61M 5/1452; A61M 2205/50; A61M 5/14244; A61M 5/142;
(Continued)

(56) References Cited

U.S. PATENT DOCUMENTS 3,701,345 A    10/1972 Heilman et al.
4,006,736 A    2/1977 Kranys et al.
(Continued)

FOREIGN PATENT DOCUMENTS

CA    3110859 A1 *  3/2020   ............ A61M 5/007
EP    2985047 A1    2/2016
(Continued)

OTHER PUBLICATIONS

"International Preliminary Report on Patentability from PCT Application No. PCT/US2020/061474", Jun. 2, 2022.

*Primary Examiner* — Andre J Allen
(74) *Attorney, Agent, or Firm* — Joseph L. Kent; James R. Stevenson; David Schramm

(57) ABSTRACT

A system, method, and computer program product are disclosed for a flow rate algorithm that utilizes changes in fluid pressure over a set time interval to calculate a true flow rate compared to a programmed flow rate, determine any over-delivery or un-der-delivery in the amount of fluid delivered over the set time interval, compensate for any determined over-delivery or under-delivery in the fluid flow rate over a subsequent set time interval, and repeat the flow rate algorithm for a series of subsequent set time intervals over the duration of a fluid injection procedure.

22 Claims, 13 Drawing Sheets

(52) U.S. Cl.
CPC ............ *A61M 2205/3334* (2013.01); *A61M 2205/502* (2013.01); *A61M 2205/70* (2013.01)

(58) Field of Classification Search
CPC ........ A61M 5/172; A61M 2005/14252; A61M 5/007; A61M 2205/502; A61M 2005/14268; A61M 5/1723; A61M 5/1413; A61M 2209/045; A61M 5/16831; A61M 5/158; A61M 5/16827; A61M 2205/18; A61M 2205/3569; A61M 2205/52; A61M 2205/583; A61M 5/16804; A61M 2205/3331; A61M 2005/14506; A61M 2205/8206; A61M 2205/3334; A61M 5/14224; A61M 5/152; A61M 5/14526; A61M 2205/3368; A61M 5/162; A61M 2205/0266; A61M 5/16886; A61M 5/16813; A61M 2230/201; A61M 2005/14208; A61M 2205/3576; A61M 5/168; A61M 5/16809; A61M 5/14216; A61M 5/14232; A61M 2005/1585; A61M 5/14212; A61M 2005/1402; A61M 2205/581; A61M 2205/3592; A61M 5/365; A61M 5/148; A61M 2205/3389; A61M 2205/8237; A61M 2205/3375; A61M 2005/1581; A61M 2005/16863; A61M 5/16881; A61M 5/1454; A61M 2005/0294; A61M 2205/3546; A61M 2205/3379; A61M 5/14276; A61M 2206/22; A61M 2005/1586; A61M 2005/1726; A61M 2205/582; A61M 2207/00; A61M 2205/3523; A61M 5/1407; A61M 2205/3306; A61M 2205/3337; A61M 5/141; A61M 5/14546; A61M 2205/04; A61M 39/10; A61M 5/5086; A61M 5/1408; A61M 2005/14513; A61M 2205/3303; A61M 2205/3341; A61M 5/3287; A61M 2005/1583; A61M 5/16854; A61M 2205/16; A61M 5/14566; A61M 5/16877; A61M 39/24; A61M 5/14; A61M 2005/3128; A61M 37/0015; A61M 2037/0023; A61M 5/1684; A61M 5/145; A61M 2205/6018; A61M 2205/332; A61M 5/19; A61M 2205/12; A61M 2005/1403; A61M 2205/3561; A61M 2205/3317; A61M 2037/0061; A61M 2205/14; A61M 39/1011; A61M 5/20; A61M 25/007; A61M 2005/14204; A61M 5/14228; A61M 2005/14553; A61M 39/22; A61M 5/31511; A61M 39/223; A61M 31/002; A61M 2205/128; A61M 2202/0007; A61M 5/3298; A61M 2205/3584; A61M 39/26; A61M 2005/3123; A61M 2205/6054; A61M 11/007; A61M 2205/6072; A61M 5/1456; A61M 2209/088; A61M 2205/197; A61M 2205/6045; A61M 39/0247; A61M 5/3129; A61M 2039/1033; A61M 2205/6063; A61M 5/1409; A61M 5/36; A61M 5/44; A61M 2209/086; A61M 31/00; A61M 2005/14573; A61M 5/288; A61M 5/32; A61M 5/322; A61M 2025/0057; A61M 1/28; A61M 39/0208; A61M 5/385; A61M 5/1626; A61M 25/0084; A61M 2039/242; A61M 25/0068; A61M 15/08; A61M 2205/70; A61M 2205/702; A61M 2039/1077; A61M 37/00; A61M 2205/3553; A61M 2205/36; A61M 2209/01; A61M 5/1422; A61M 2210/0612; A61M 2210/0662; A61M 2005/1623; A61M 35/003; A61M 11/005; A61M 2039/1072; A61M 2230/005; A61M 5/30; A61M 5/3158; A61M 5/24; A61M 5/31525; A61M 2205/3393; A61M 39/12; A61M 2039/229; A61M 3/022; A61M 5/14593; A61M 2005/1405; A61M 2205/07; A61M 25/0023; A61M 2005/14264; A61M 2005/14256; A61M 2037/003; A61M 1/1601; A61M 2039/1027; A61M 2205/505; A61M 5/1411; A61M 5/2033; A61M 5/3232; A61M 5/3234; A61M 11/00; A61M 2025/0073; A61M 2205/3355; A61M 2205/3386; A61M 2205/8212; A61M 5/427; A61M 2205/123; A61M 2205/3344; A61M 2205/60; A61M 2037/0053; A61M 2205/276; A61M 5/155; A61M 5/3146; A61M 2205/6009; A61M 5/284; A61M 3/0208; A61M 39/04; A61M 5/002; A61M 5/16859; A61M 2205/6081; A61M 2205/7536; A61M 2005/1787; A61M 2205/33; A61M 5/00; A61M 15/009; A61M 5/28; A61M 1/1561; A61M 2005/1426; A61M 2205/6027; A61M 2210/04; A61M 5/1483; A61M 5/31596; A61M 5/31513; A61M 2005/1588; A61M 2205/59; A61M 3/0202; A61M 3/0541; A61M 1/159; A61M 5/1782; A61M 1/155; A61M 2005/3114; A61M 25/00; A61M 5/1415; A61M 5/31; A61M 5/315; A61M 25/0026; A61M 3/0258; A61M 2005/206; A61M 2025/0039; A61M 25/10; A61M 5/3202; A61M 2039/025; A61M 2205/0244; A61M 2025/0004; A61M 2025/1086; A61M 2205/0216; A61M 5/14236; A61M 2039/1088; A61M 2205/3515; A61M 2230/50; A61M 25/0097; A61M 25/0108; A61M 39/105; A61M 5/31526; A61M 2005/208; A61M 2039/2473; A61M 2202/0468; A61M 35/00; A61M 5/178; A61M 5/38; A61M 15/0085; A61M 2039/1083; A61M 2039/226; A61M 2205/3327; A61M 1/14; A61M 15/0003; A61M 2039/0205; A61M 2205/82; A61M 2210/0618; A61M 3/0245; A61M 2037/0046; A61M 25/0082; A61M 2005/1587; A61M 2025/0087; A61M 2205/3365; A61M 2210/0693; A61M 1/77; A61M 2005/3117; A61M 2205/7518; A61M 2210/0625; A61M 2205/0288; A61M 2250/00; A61M 39/08; A61M 39/16; A61M 5/31551; A61M 2005/16868; A61M 2202/04; A61M 5/008; A61M 5/2066; A61M 5/3291; A61M 2205/13; A61M 2205/8281; A61M 3/0254; A61M 5/3221; A61M 5/484; A61M 2039/1066; A61M 2205/8231; A61M 2230/04; A61M 1/1565; A61M 2025/091; A61M 39/281;

A61M 2005/2474; A61M 2202/0208;
A61M 2230/63; A61M 25/0043; A61M
25/0105; A61M 39/20; A61M 1/3496;
A61M 1/92; A61M 2039/0229; A61M
2205/15; A61M 25/005; A61M 25/09;
A61M 3/0279; A61M 5/2425; A61M
2205/3606; A61M 25/0662; A61M
3/0201; A61M 39/165; A61M 1/152;
A61M 1/154; A61M 2039/0241; A61M
2202/0482; A61M 25/0045; A61M 39/28;
A61M 5/31533; A61M 1/168; A61M
2005/2073; A61M 2210/0668; A61M
5/46; A61M 5/50; A61M 2005/1416;
A61M 2039/0276; A61M 2039/2433;
A61M 2205/3351; A61M 1/85; A61M
11/001; A61M 2005/3115; A61M
39/0027; A61M 2205/3507; A61M
2205/6036; A61M 2206/20; A61M
2210/1433; A61M 16/0616; A61M
16/0683; A61M 2005/1406; A61M
2205/121; A61M 2205/587; A61M
2210/125; A61M 25/0074; A61M 5/3134;
A61M 5/31578; A61M 60/148; A61M
60/178; A61M 60/237; A61M 2021/0066;
A61M 2021/0072; A61M 2025/0089;
A61M 2205/3396; A61M 2205/35; A61M
2205/3653; A61M 2206/10; A61M
2210/1067; A61M 2210/1475; A61M
25/0102; A61M 35/30; A61M 37/0092;
A61M 5/282; A61M 5/3159; A61M
1/777; A61M 2005/16872; A61M
2005/247; A61M 2039/0238; A61M
2039/2406; A61M 2039/267; A61M
2202/0464; A61M 2210/1003; A61M
25/003; A61M 3/0212; A61M 31/005;
A61M 5/31515; A61M 2005/3103; A61M
2025/1052; A61M 2039/0009; A61M
2039/009; A61M 2039/2486; A61M
2205/585; A61M 2209/04; A61M 3/0262;
A61M 5/204; A61M 5/31568; A61M
2025/0036; A61M 25/0075; A61M
25/104; A61M 39/288; A61M 2025/004;
A61M 2039/248; A61M 2039/2493;
A61M 2230/30; A61M 39/14; A61M
5/3294; A61M 15/0065; A61M
2037/0007; A61M 2039/1038; A61M
2205/273; A61M 2209/06; A61M
25/1002; A61M 39/00; A61M 1/288;
A61M 1/72; A61M 1/743; A61M 19/00;
A61M 2005/2407; A61M 2005/31588;
A61M 2025/09175; A61M 2039/0072;
A61M 2205/3362; A61M 5/31576; A61M
5/3295; A61M 1/1621; A61M 1/1656;
A61M 15/0028; A61M 2025/0681; A61M
2205/42; A61M 2205/75; A61M
2205/7527; A61M 35/006; A61M 5/1424;
A61M 5/16895; A61M 5/283; A61M
5/3145; A61M 5/347; A61M 1/153;
A61M 1/84; A61M 16/0875; A61M
2005/3223; A61M 2005/3224; A61M
2005/3226; A61M 2005/3228; A61M
2005/323; A61M 2005/3235; A61M
2005/3236; A61M 2005/3239; A61M
2005/3241; A61M 2025/0002; A61M
25/04; A61M 5/3156; A61M 5/3157;
A61M 1/282; A61M 1/3643; A61M
2005/314; A61M 2005/31516; A61M
2205/186; A61M 2205/3613; A61M
25/0147; A61M 39/18; A61M 39/227;
A61M 39/284; A61M 5/31541; A61M
1/982; A61M 2205/364; A61M 25/0069;
A61M 25/0606; A61M 5/2053; A61M
5/2448; A61M 1/90; A61M 2005/2026;
A61M 2039/167; A61M 2205/126; A61M
2205/3313; A61M 2205/368; A61M
25/1011; A61M 5/3007; A61M 5/3148;
A61M 5/31535; A61M 1/1524; A61M
11/042; A61M 16/06; A61M 2005/2488;
A61M 2025/09083; A61M 2025/09091;
A61M 2039/2453; A61M 2205/8262;
A61M 25/09033; A61M 5/1486; A61M
5/329; A61M 5/425; A61M 13/003;
A61M 16/024; A61M 2005/14533; A61M
2025/0183; A61M 2039/027; A61M
2205/0277; A61M 2209/08; A61M
2230/06; A61M 25/0032; G01F 22/00;
G01F 11/086; G01F 11/022; G01F
11/029; G01F 1/8413; G01F 1/8422;
G01F 1/8495; G01F 25/0092; G01F
25/10; G01F 11/021; G01F 1/74; G01F
15/08; G01F 25/0084; G01F 1/696; G01F
1/708; G01F 15/063; G01F 25/17; G01F
17/00; G01F 1/34; G01F 5/005; G01F
13/00; G01F 25/00; G01F 1/206; G01F
1/66; G01F 1/8445; G01F 19/00; G01F
3/00; G01F 23/00; G01F 1/36; G01F
1/8472; G01F 11/02; G01F 11/04; G01F
11/08; G01F 22/02; G01F 1/662; G01F
13/006; G01F 1/007; G01F 1/667; G01F
15/005; G01F 1/00; G01F 11/027; G01F
11/082; G01F 23/14; G01F 23/242; G01F
1/363; G01F 1/661; G01F 1/72; G01F
11/024; G01F 11/16; G01F 15/06; G01F
3/20; G01F 1/58; G01F 1/7086; G01F
1/86; G01F 11/023; G01F 11/262; G01F
11/263; G01F 11/284; G01F 15/007;
G01F 23/26; G01F 3/10; G01F 3/227;
G01F 1/10; G01F 1/103; G01F 1/56;
G01F 1/64; G01F 1/6842; G01F 1/698;
G01F 1/6986; G01F 1/7044; G01F 1/76;
G01F 1/88; G01F 11/00; G01F 11/28;
G01F 11/38; G01F 15/001; G01F 15/003;
G01F 15/02; G01F 15/028; G01F
23/0015; G01F 23/263; G01F 3/18

See application file for complete search history.

(56) References Cited

U.S. PATENT DOCUMENTS

| | | | |
|---|---|---|---|
| 7,553,294 B2 | 6/2009 | Lazzaro et al. | |
| 7,563,249 B2 | 7/2009 | Schriver et al. | |
| 8,414,522 B2* | 4/2013 | Kamen | A61B 5/15117 604/890.1 |
| 8,439,863 B2 | 5/2013 | Fago et al. | |
| 8,945,051 B2 | 2/2015 | Schriver et al. | |
| 9,173,995 B1 | 11/2015 | Tucker et al. | |
| 9,242,083 B2 | 1/2016 | Fago et al. | |
| 10,124,110 B2 | 11/2018 | Dedig et al. | |
| 10,507,319 B2 | 12/2019 | Haury et al. | |
| 10,549,084 B2 | 2/2020 | Sokolov et al. | |
| 10,583,256 B2 | 3/2020 | Berry et al. | |
| 11,141,535 B2* | 10/2021 | Uber, III | A61M 5/3221 |

(56) References Cited

U.S. PATENT DOCUMENTS

| | | | |
|---|---|---|---|
| 2004/0015124 A1 | | 1/2004 | Sciulli et al. |
| 2009/0093774 A1 | * | 4/2009 | Wang ................ A61M 5/16881 |
| | | | 604/247 |
| 2009/0113996 A1 | * | 5/2009 | Wang .................... G01N 11/08 |
| | | | 73/54.43 |
| 2011/0137241 A1 | | 6/2011 | Delcastilio et al. |
| 2012/0150356 A1 | * | 6/2012 | Crivelli .................... F16K 1/34 |
| | | | 700/282 |
| 2014/0088555 A1 | | 3/2014 | Li et al. |
| 2014/0224829 A1 | | 8/2014 | Capone et al. |
| 2014/0276550 A1 | | 9/2014 | Uram et al. |
| 2015/0190573 A1 | | 7/2015 | Moberg et al. |
| 2016/0331951 A1 | | 11/2016 | Sokolov et al. |
| 2017/0035974 A1 | | 2/2017 | Berry et al. |
| 2018/0161496 A1 | | 6/2018 | Berry et al. |
| 2018/0221575 A1 | | 8/2018 | Wolff |

FOREIGN PATENT DOCUMENTS

| | | | |
|---|---|---|---|
| WO | 2013176770 A2 | 11/2013 | |
| WO | 2016112163 A1 | 7/2016 | |
| WO | 2019046299 A1 | 3/2019 | |
| WO | 2019204605 A1 | 10/2019 | |
| WO | WO-2021247595 A1 * | 12/2021 | ............ A61M 5/007 |

* cited by examiner

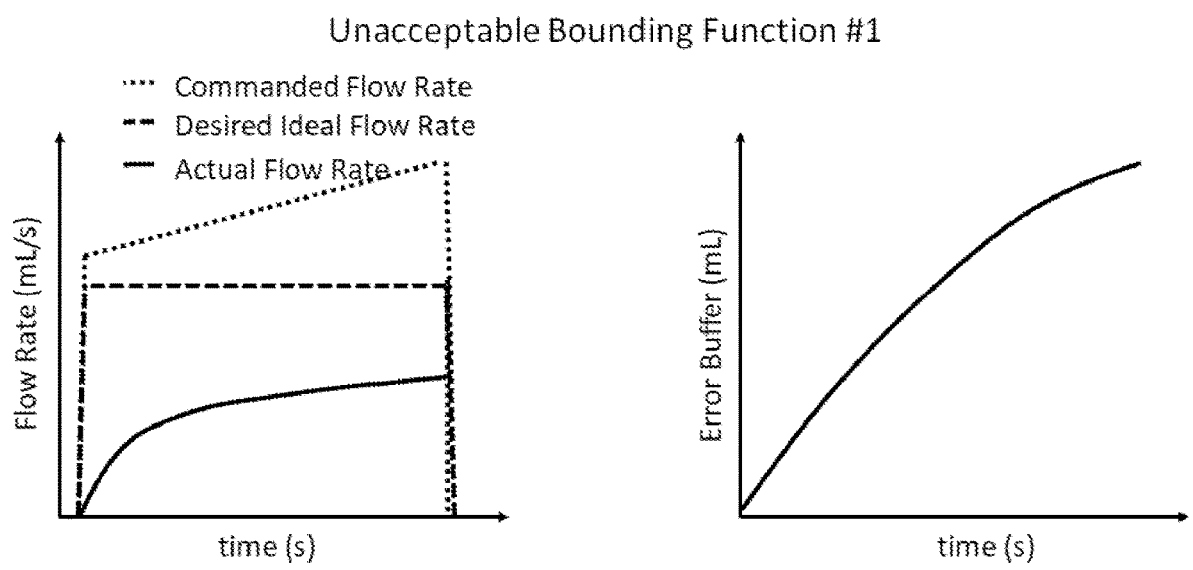
FIG. 11A  FIG. 11B
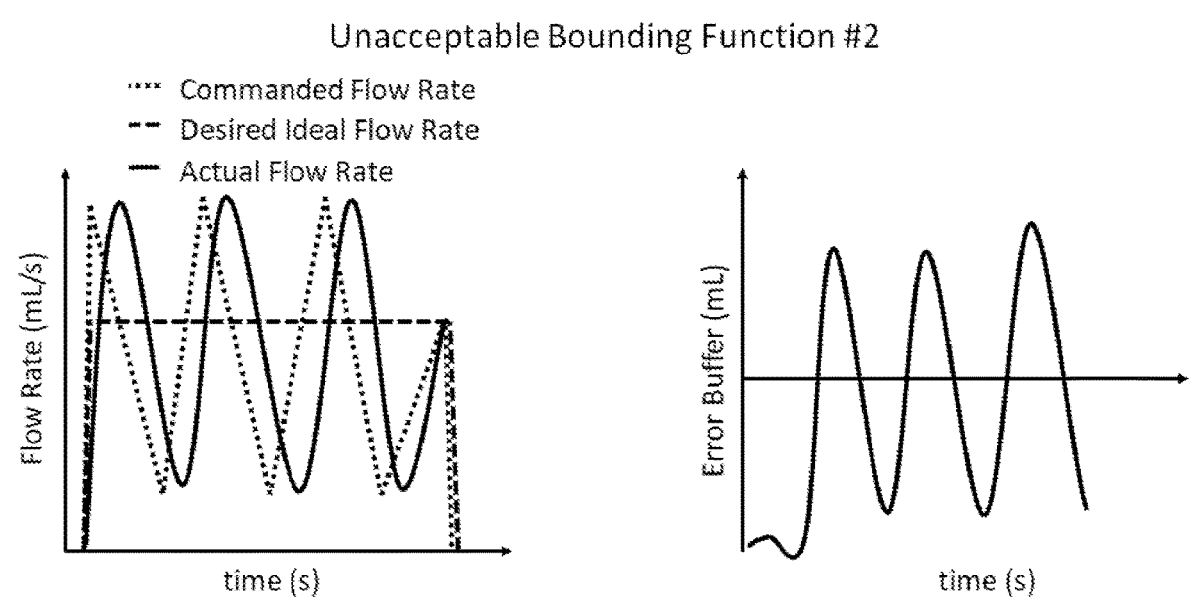
FIG. 12A  FIG. 12B

SYSTEM AND METHOD FOR FLUID DELIVERY USING PRESSURE-BASED MOTOR CONTROL FOR FLUID INJECTOR DEVICES

CROSS-REFERENCE TO RELATED APPLICATION

This application is a U.S. national phase application under 35 U.S.C. § 371 of PCT International Application No. PCT/US2020/061474, filed 20 Nov. 2020, and claims priority to U.S. Provisional Application No. 63/938,397, filed 21 Nov. 2019, the disclosure disclosures of which are incorporated by reference herein in their entirety.

BACKGROUND OF THE DISCLOSURE

1. Field of the Disclosure

This disclosure relates generally to systems, devices, products, apparatus, and methods that are used for improved fluid delivery using real-time, pressure-based control of one or more drive components of a fluid injector during a fluid injection procedure.

2. Description of the Relevant Background

In many medical diagnostic and therapeutic procedures, a medical practitioner, such as a physician or radiologist, injects a patient with one or more fluids using a powered fluid injector system. A number of powered fluid injector systems for pressurized injection of fluids have been developed for use in procedures such as angiography, computed tomography (CT), molecular imaging (such as PET imaging), and magnetic resonance imaging (MRI).

An actual flow rate (or delivered volume) of fluid that is delivered to the patient is targeted to be as close as possible to the programmed flow rate (or desired volume). However, the actual performance of the fluid delivery system is a function of many factors due to overall impedance, compliance, and capacitance of the fluid delivery system, such as pressure induced swelling of fluid path components and mechanical slack within the system. In certain delivery procedures, impedance, compliance, and capacitance of the fluid delivery system may cause a fluid flow over-rate or under-rate (or volume over- or under-delivery) from a programmed flow rate (or desired volume). Further, there are inherent interactions between two or more fluids that have different fluid properties (e.g. viscosity, density, bulk modulus) which can cause anomalies in flow rate out of the injector as compared to flow rate set by the injector. The combination of these various interactions cannot readily be modeled into characterizations of the compliance of the fluid delivery system.

Existing injector systems and protocols fail to address the under-delivery or over-delivery of fluid resulting from system impedance, compliance, and/or capacitance. As a result, less than optimal injection boluses may occur and/or fluid delivery procedures may cause relatively large amounts of wasted fluid, and/or under-delivery of fluid to a patient. Accordingly, there is a need in the art to improve fluid delivery profiles during fluid injection procedures using fluid injection devices so that optimum fluid delivery is obtained.

SUMMARY OF THE DISCLOSURE

Accordingly, provided are systems, devices, products, apparatus, and/or methods for a fluid injector system having improved fluid delivery by real-time control of a fluid injector motor in response to changes in pressure of fluid within an injection reservoir. Embodiments of the present disclosure allow for improved dose efficiency for contrast agent delivery and similar imaging quality with reduced contrast volume due to accuracy of contrast delivery.

According to non-limiting embodiments, a fluid injector system for use in administering at least one fluid to a patient is described. The fluid injector system may include a memory for storing therein a programmed flow rate to be delivered during execution of a fluid delivery procedure using a fluid injector and a maximum allowable deviation in the programmed flow rate. The fluid injector further may include at least one sensor for measuring a pressure of the at least one fluid, wherein the pressure is generated by at least one drive component of the fluid injector during execution of the fluid delivery procedure. The fluid injector further may include a control device operatively associated with the at least one drive component of the fluid injector, the control device including at least one processor programmed or configured to perform an operation. According to embodiments, the at least one sensor may measure the pressure by a strain on a motor of at least one drive component, for example by measuring a current of a motor. The operation may include determining an actual flow rate during a specified time interval of the fluid delivery procedure based on a change in pressure measured by the at least one sensor over the specified time interval, determining a deviation of the actual flow rate from the programmed flow rate over the specified time interval, and calculating a new programmed flow rate for a subsequent time interval after the specified time interval based on the programmed flow rate and the deviation of the actual flow rate from the programmed flow rate over the specified time interval.

In accordance with some non-limiting embodiments, the control device including at least one processor may be further programmed or configured to perform an operation including comparing the maximum allowable deviation to the deviation of the actual flow rate from the programmed flow rate over the specified time interval to determine a flow rate correction, and calculating the new programmed flow rate for the subsequent time interval based on the programmed flow rate and the flow rate correction.

In accordance with some non-limiting embodiments, the deviation of the actual flow rate from the programmed flow rate may be limited by predetermined bounds. In accordance with some non-limiting embodiments, the flow rate correction may be equal to the maximum allowable deviation if the deviation of the actual flow rate from the programmed flow rate is greater than the maximum allowable deviation. In accordance with some non-limiting embodiments, a difference between the deviation of the actual flow rate from the programmed flow rate and the maximum allowable deviation may be stored as a buffer deviation for use in determining a new flow rate correction in one or more subsequent time intervals after the second time interval. In accordance with some non-limiting embodiments, the flow rate correction may be equal to the actual flow rate if the deviation of the actual flow rate from the programmed flow rate is less than or equal to the maximum allowable deviation.

In accordance with some non-limiting embodiments, wherein the control device is configured to use a machine learning model designed to receive, as an input, data associated with the fluid injection procedure, and provide, as an output, instructions to drive the one or more drive components to deliver a desired volume of fluid at the programmed flow rate.

In accordance with some non-limiting embodiments, the operation to determine the actual flow rate during the specified time interval may include measuring a first pressure using the at least one sensor at a beginning of the specified time interval and measuring a second pressure using the at least one sensor at an end of the specified time interval and converting the first pressure and the second pressure to a change in pressure corresponding to the actual flow rate during the specified time interval.

In accordance with some non-limiting embodiments, the change in pressure may be based on a difference between the second pressure and the first pressure, and at least one scaling factor that is determined by one or more features of the fluid injector.

In accordance with some non-limiting embodiments, the at least one sensor may be a force sensor for measuring a force output of the at least one drive component. In accordance with some non-limiting embodiments, the at least one sensor may be a pressure sensor associated with a fluid reservoir or a fluid path component of the fluid injector. According to certain non-limiting embodiments, the at least one sensor may be a current sensor measuring a current of a motor associated with the at least one drive component.

In accordance with some non-limiting embodiments, the flow rate correction for each subsequent time interval may be based on a difference between the maximum allowable deviation and the deviation of the actual flow rate from the new programmed flow rate over each subsequent time interval, and a buffer deviation from at least one previous time interval.

In accordance with some non-limiting embodiments, the operation performed by the control device further may include the operation to repeat steps (a)-(c) for each subsequent time interval in the fluid injection procedure, wherein the new programmed flow rate is used as the programmed flow rate. In accordance with some non-limiting embodiments, the operation performed by the control device further may include delivering the fluid at the new programmed flow rate in the subsequent time interval.

In accordance with some non-limiting embodiments, a computer-implemented method for monitoring performance of a fluid injector system for use in administering at least one fluid to a patient may include (a) storing, in a memory device, a programmed flow rate for the fluid to be delivered and a maximum allowable deviation in the programmed flow rate during a fluid delivery procedure using a fluid injector; (b) measuring, using at least one sensor, a pressure of the at least one fluid generated by at least one drive component of the fluid injector during execution of the fluid delivery procedure; (c) determining, with a control device comprising at least one processor, an actual flow rate during a specified time interval of the fluid delivery procedure based on a change in pressure measured by the at least one sensor over the specified time interval; (d) determining, with the control device, a deviation of the actual flow rate from the programmed flow rate over the specified time interval; (e) calculating, with the control device, a new programmed flow rate for at least one subsequent time interval after the specified time interval based on the programmed flow rate and the deviation of the actual flow rate from the programmed flow rate over the specified time interval.

In accordance with some non-limiting embodiments, the method further may include comparing, with the control device, the maximum allowable deviation to the deviation of the actual flow rate from the programmed flow rate over the specified time interval to determine a flow rate correction, and calculating the new programmed flow rate for the subsequent time interval based on the programmed flow rate and the flow rate correction.

In accordance with some non-limiting embodiments, the method further may include repeating steps (c)-(e) for each subsequent time interval in the fluid injection procedure, wherein the new programmed flow rate is used as the programmed flow rate. In accordance with some non-limiting embodiments, the method further may include delivering the fluid at the new programmed flow rate in the subsequent time interval.

In accordance with some non-limiting embodiments, a computer program product is provided for controlling operation of a fluid injector system for use in administering at least one fluid to a patient. The computer program product may include at least one non-transitory computer-readable medium having one or more instructions that, when executed by at least one processor, cause the at least one processor to: determine an actual flow rate for the fluid during a specified time interval of a fluid delivery procedure based on a change in pressure generated by at least one drive component of the fluid injector during the fluid delivery procedure and measured by at least one sensor over the specified time interval; determine, with a control device operatively associated with the at least one drive component of the fluid injector, a deviation of the actual flow rate from the programmed flow rate over the specified time interval; and calculate a new programmed flow rate for at least one subsequent time interval after the specified time interval based on the programmed flow rate and the deviation of the actual flow rate from the programmed flow rate over the specified time interval.

In accordance with some non-limiting embodiments, the computer program product further may include one or more instructions that, when executed by the at least one processor, cause the at least one processor to compare, with the control device, a maximum allowable deviation to the deviation of the actual flow rate from the programmed flow rate over the specified time interval to determine a flow rate correction, and calculate, with the control device, the new programmed flow rate for the subsequent time interval after the specified time interval based on the programmed flow rate and the flow rate correction.

In accordance with some non-limiting embodiments, the computer program product further may include repeating steps (a)-(c) for each subsequent time interval in the fluid injection procedure, wherein the new programmed flow rate is used as the programmed flow rate. In accordance with some non-limiting embodiments, the computer program product further may include delivering the fluid at the new programmed flow rate in the subsequent time interval.

Further embodiments of the present disclosure are characterized in one or more of the following clauses:

Clause 1. A fluid injector system configured for use in administering at least one fluid to a patient, the fluid injector system comprising: a memory for storing therein a programmed flow rate to be delivered during execution of a fluid delivery procedure using a fluid injector and a maximum allowable deviation in the programmed flow rate; at least one sensor configured for measuring a pressure of the at least one fluid, wherein the pressure is generated by at least one drive component of the fluid injector during execution of the fluid delivery procedure; and a control device operatively associated with the at least one drive component of the fluid injector, the control device including at least one processor programmed or configured to perform an operation comprising: determining an actual flow rate during a specified time interval of the fluid delivery procedure based on a change in pressure measured by the at least one sensor over the specified time interval; determining a deviation of the actual flow rate from the programmed flow rate over the specified time interval; and calculating a new programmed flow rate for a subsequent time interval after the specified time interval based on the programmed flow rate and the deviation of the actual flow rate from the programmed flow rate over the specified time interval.

Clause 2. The fluid injector system of clause 1, wherein the control device including the at least one processor is further programmed or configured to perform an operation comprising comparing the maximum allowable deviation to the deviation of the actual flow rate from the programmed flow rate over the specified time interval to determine a flow rate correction, and calculating the new programmed flow rate for the subsequent time interval based on the programmed flow rate and the flow rate correction.

Clause 3. The fluid injector system of clause 1 or clause 2, wherein the deviation of the actual flow rate from the programmed flow rate is limited by predetermined bounds.

Clause 4. The fluid injector system of clause 2 or clause 3, wherein the flow rate correction is equal to the maximum allowable deviation if the deviation of the actual flow rate from the programmed flow rate is greater than the maximum allowable deviation.

Clause 5. The fluid injector system of clause 4, wherein a difference between the deviation of the actual flow rate from the programmed flow rate and the maximum allowable deviation is stored as a buffer deviation for use in determining a new flow rate correction in one or more subsequent time intervals after the second time interval.

Clause 6. The fluid injector system of any of clauses 2-5, wherein the flow rate correction is equal to the actual flow rate if the deviation of the actual flow rate from the programmed flow rate is less than or equal to the maximum allowable deviation.

Clause 7. The fluid injector system of any of clauses 2-6, wherein the control device is configured to use a machine learning model designed to receive, as an input, data associated with the fluid injection procedure, and provide, as an output, instructions to drive the one or more drive components to deliver a desired volume of fluid at the programmed flow rate.

Clause 8. The fluid injector system of any of clauses 1-7, wherein the operation to determine the actual flow rate during the specified time interval comprises measuring a first pressure using the at least one sensor at a beginning of the specified time interval and measuring a second pressure using the at least one sensor at an end of the specified time interval and converting the first pressure and the second pressure to a change in pressure corresponding to the actual flow rate during the specified time interval.

Clause 9. The fluid injector system of clause 8, wherein the change in pressure is based on a difference between the second pressure and the first pressure, and at least one scaling factor that is determined by one or more features of the fluid injector.

Clause 10. The fluid injector system of any of clauses 1-9, wherein the at least one sensor is a force sensor configured for measuring a force output of the at least one drive component.

Clause 11. The fluid injector system of any of clauses 1-9, wherein the at least one sensor is a pressure sensor associated with a fluid reservoir or a fluid path component of the fluid injector.

Clause 12. The fluid injector system of any of clauses 2-11, wherein the flow rate correction for each subsequent time interval is based on a difference between the maximum allowable deviation and the deviation of the actual flow rate from the new programmed flow rate over each subsequent time interval, and a buffer deviation from at least one previous time interval.

Clause 13. The fluid injector system of any of clauses 1-12, wherein the operation performed by the control device further comprises the operation to repeat steps (a)-(c) for each subsequent time interval in the fluid injection procedure, wherein the new programmed flow rate is used as the programmed flow rate.

Clause 14. The fluid injector system of any of clauses 1-13, wherein the operation performed by the control device further comprises delivering the fluid at the new programmed flow rate in the subsequent time interval.

Clause 15. A computer-implemented method for monitoring performance of a fluid injector system configured for use in administering at least one fluid to a patient, the method comprising: (a) storing, in a memory device, a programmed flow rate for the fluid to be delivered and a maximum allowable deviation in the programmed flow rate during a fluid delivery procedure using a fluid injector; (b) measuring, using at least one sensor, a pressure of the at least one fluid generated by at least one drive component of the fluid injector during execution of the fluid delivery procedure; (c) determining, with a control device comprising at least one processor, an actual flow rate during a specified time interval of the fluid delivery procedure based on a change in pressure measured by the at least one sensor over the specified time interval; (d) determining, with the control device, a deviation of the actual flow rate from the programmed flow rate over the specified time interval; (e) calculating, with the control device, a new programmed flow rate for a subsequent time interval after the specified time interval based on the programmed flow rate and the deviation of the actual flow rate from the programmed flow rate over the specified time interval.

Clause 16. The computer-implemented method of clause 15, further comprising comparing, with the control device, the maximum allowable deviation to the deviation of the actual flow rate from the programmed flow rate over the specified time interval to determine a flow rate correction, and calculating the new programmed flow rate for the subsequent time interval based on the programmed flow rate and the flow rate correction.

Clause 17. The computer-implemented method of clause 15 or 16, wherein the deviation of the actual flow rate from the programmed flow rate is limited by predetermined bounds.

Clause 18. The computer-implemented method of clause 16 or 17, wherein the flow rate correction is equal to the maximum allowable deviation if the deviation of the actual flow rate from the programmed flow rate is greater than the maximum allowable deviation.

Clause 19. The computer-implemented method of clause 18, wherein a difference between the deviation of the actual flow rate from the programmed flow rate and the maximum allowable deviation is stored as a buffer deviation for use in determining a new flow rate correction in one or more subsequent time intervals after the second time interval.

Clause 20. The computer-implemented method of any of clauses 16-19, wherein the flow rate correction is equal to the actual flow rate if the deviation of the actual flow rate from the programmed flow rate is less than or equal to the maximum allowable deviation.

Clause 21. The computer-implemented method of any of clauses 16-20, wherein the control device is configured to use a machine learning model designed to receive, as an input, data associated with the fluid injection procedure, and provide, as an output, instructions to drive the one or more drive components to deliver a desired volume of fluid at the programmed flow rate.

Clause 22. The computer-implemented method of any of clauses 15-21, wherein determining the actual flow rate during the specified time interval comprises measuring a first pressure using the at least one sensor at a beginning of the specified time interval and measuring a second pressure using the at least one sensor at an end of the specified time interval and converting the first pressure and the second pressure to a change in pressure corresponding to the actual flow rate during the specified time interval.

Clause 23. The computer-implemented method of clause 22, wherein the change in pressure is based on a difference between the second pressure and the first pressure, and at least one scaling factor that is determined by one or more features of the fluid injector.

Clause 24. The computer-implemented method of any of clauses 15-23, wherein the at least one sensor is a force sensor configured for measuring a force output of the at least one drive component.

Clause 25. The computer-implemented method of any of clauses 15-23, wherein the at least one sensor is a pressure sensor associated with a fluid reservoir or a fluid path component of the fluid injector.

Clause 26. The computer-implemented method of any of clauses 15-25, wherein the flow rate correction for each subsequent time interval is based on a difference between the maximum allowable deviation and the deviation of the actual flow rate from the new programmed flow rate over each subsequent time interval, and a buffer deviation from at least one previous time interval.

Clause 27. The computer-implemented method of any of clauses 15-26, further comprising repeating steps (c)-(e) for each subsequent time interval in the fluid injection procedure, wherein the new programmed flow rate is used as the programmed flow rate.

Clause 28. The computer-implemented method of any of clauses 15-27, further comprising delivering the fluid at the new programmed flow rate in the subsequent time interval.

Clause 29. A computer program product for controlling operation of a fluid injector system configured for use in administering at least one fluid to a patient, the computer program product comprising at least one non-transitory computer-readable medium comprising one or more instructions that, when executed by at least one processor, cause the at least one processor to: determine an actual flow rate for the fluid during a specified time interval of a fluid delivery procedure based on a change in pressure generated by at least one drive component of the fluid injector during the fluid delivery procedure and measured by at least one sensor over the specified time interval; determine, with a control device operatively associated with the at least one drive component of the fluid injector, a deviation of the actual flow rate from the programmed flow rate over the specified time interval; and calculate, with the control device, a new programmed flow rate for a subsequent time interval after the specified time interval based on the programmed flow rate and the deviation of the actual flow rate from the programmed flow rate over the specified time interval.

Clause 30. The computer program product of clause 29, further comprising one or more instructions that, when executed by the at least one processor, cause the at least one processor to compare, with the control device, a maximum allowable deviation to the deviation of the actual flow rate from the programmed flow rate over the specified time interval to determine a flow rate correction, and calculate, with the control device, the new programmed flow rate for the subsequent time interval after the specified time interval based on the programmed flow rate and the flow rate correction.

Clause 31. The computer program product of clause 29 or 30, wherein the deviation of the actual flow rate from the programmed flow rate is limited by predetermined bounds.

Clause 32. The computer program product of clause 30 or 31, wherein the flow rate correction is equal to the maximum allowable deviation if the deviation of the actual flow rate from the programmed flow rate is greater than the maximum allowable deviation.

Clause 33. The computer program product of clause 32, wherein a difference between the deviation of the actual flow rate from the programmed flow rate and the maximum allowable deviation is stored as a buffer deviation for use in determining a new flow rate correction in one or more subsequent time intervals after the second time interval.

Clause 34. The computer program product of any of clauses 30-33, wherein the flow rate correction is equal to the actual flow rate if the deviation of the actual flow rate from the programmed flow rate is less than or equal to the maximum allowable deviation.

Clause 35. The computer program product of any of clauses 29-34, wherein the control device is configured to use a machine learning model designed to receive, as an input, data associated with the fluid injection procedure, and provide, as an output, instructions to drive the one or more drive components to deliver a desired volume of fluid at the programmed flow rate.

Clause 36. The computer program product of any of clauses 29-35, wherein determining the actual flow rate during the specified time interval comprises measuring a first pressure using the at least one sensor at a beginning of the specified time interval and measuring a second pressure using the at least one sensor at an end of the specified time interval and converting the first pressure and the second pressure to a change in pressure corresponding to the actual flow rate during the specified time interval.

Clause 37. The computer program product of clause 36, wherein the change in pressure is based on a difference between the second pressure and the first pressure, and at least one scaling factor that is determined by one or more features of the fluid injector.

Clause 38. The computer program product of any of clauses 29-37, wherein the at least one sensor is a force sensor configured for measuring a force output of the at least one drive component.

Clause 39. The computer program product of any of clauses 29-37, wherein the at least one sensor is a pressure sensor associated with a fluid reservoir or a fluid path component of the fluid injector.

Clause 40. The computer program product of any of clauses 30-39, wherein the flow rate correction for each subsequent time interval is based on a difference between the maximum allowable deviation and the deviation of the actual flow rate from the new programmed flow rate over each subsequent time interval, and a buffer deviation from at least one previous time interval.

Clause 41. The computer program product of any of clauses 29-40, further comprising repeating steps (a)-(c) for each subsequent time interval in the fluid injection procedure, wherein the new programmed flow rate is used as the programmed flow rate.

Clause 42. The computer program product of any of clauses 29-41, further comprising delivering the fluid at the new programmed flow rate in the subsequent time interval.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

Additional advantages and details of the disclosure are explained in greater detail below with reference to the exemplary embodiments that are illustrated in the accompanying schematic figures, in which:

FIG. 11A is a graph showing a change in flow rate as a function of time for an unacceptable bounding function in accordance with a first example;

FIG. 11B is a graph of an error buffer (in ml) as a function of time for the unacceptable bounding function shown in FIG. 11A;

FIG. 12A is a graph showing a change in flow rate as a function of time for an unacceptable bounding function in accordance with a second example;

FIG. 12B is a graph of an error buffer (in ml) as a function of time for the unacceptable bounding function shown in FIG. 12A;

In FIGS. 1 to 16, like characters refer to the same components and elements, as the case may be, unless otherwise stated.

Figure 1:
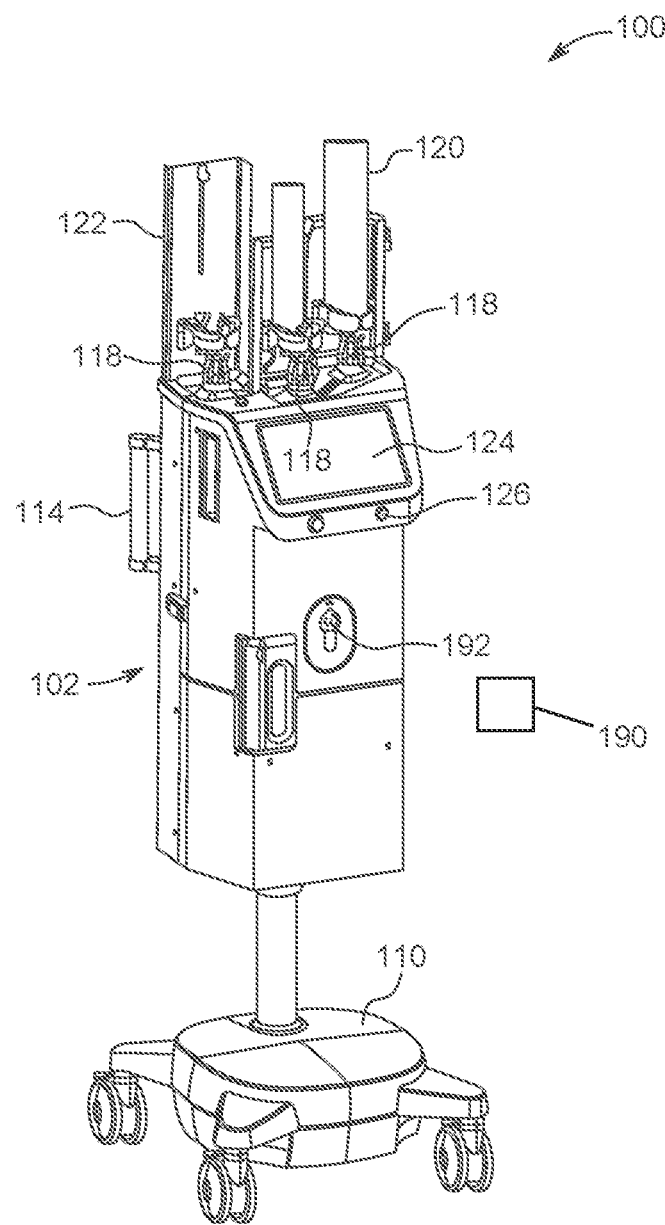
FIG. 1 is a perspective view of a fluid injector system according to one example of the present disclosure.

It is to be expressly understood, however, that the drawings are for the purpose of illustration and description only and are not intended as a definition of the limits of the disclosure.

DETAILED DESCRIPTION OF THE DISCLOSURE

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston for delivering fluid from a syringe. Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The terms "approximately", "about", and "substantially" mean a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting. In the present document, the word "exemplary" is used herein to mean "serving as an example, instance, or illustration." Any embodiment or implementation of the present subject matter described herein as "exemplary" is not necessarily to be construed as preferred over other embodiments.

The terms "first", "second", and the like, or a), b), c) etc. are not intended to refer to any particular order or chronology, but refer to different conditions, properties, or elements. The term "at least" is synonymous with "greater than or equal to." Various described operations may be performed in a different order, modified, or removed. Moreover, steps may be added to described methods and still conform to the described embodiments. Further, operations described herein may occur sequentially or certain operations may be processed in parallel.

When used in relation to a fluid reservoir, such as a syringe or multiple syringe disposable set, the term "distal" refers to a portion of the fluid reservoir nearest to a patient. When used in relation to a fluid reservoir, such as a syringe or multiple syringe disposable set, the term "proximal" refers to a portion of the fluid reservoir nearest to the injector system.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In certain embodiments, a message may refer to a network packet (e.g., a data packet and/or the like) that includes data. It will be appreciated that numerous other arrangements are possible.

As used herein, the term "server" may refer to one or more computing devices, such as processors, storage devices, and/or similar computer components that communicate with client devices and/or other computing devices over a network, such as the Internet or private networks, and, in some examples, facilitate communication among other servers and/or client devices. It will be appreciated that various other arrangements are possible. As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

The terms "comprises", "comprising", or any other variations thereof, are intended to cover a non-exclusive inclusion, such that a setup, device, or method that comprises a list of components or steps does not include only those components or steps but may include other components or steps not expressly listed or inherent to such setup, device, or method. In other words, one or more elements in a system or apparatus proceeded by "comprises . . . a" does not, without more constraints, preclude the existence of other elements or additional elements in the system or method. The terms "includes", "including", or any other variations thereof are intended to cover a non-exclusive inclusion such that a setup, device, or method that includes a list of components or steps does not include only those components or steps but may include other components or steps not expressly listed or inherent to such setup, device, or method. In other words, one or more elements in a system or apparatus proceeded by "includes . . . a" does not, without more constraints, preclude the existence of other elements or additional elements in the system or method.

The terms "embodiment", "embodiments", "one or more embodiments", "some non-limiting embodiments", and "one embodiment" mean "one or more (but not all) embodiments of the present disclosure" unless expressly specified otherwise. A description of an embodiment with several components in communication with each other does not imply that all such components are required. To the contrary, a variety of optional components are described to illustrate the wide variety of possible embodiments of the disclosure.

No aspect, component, element, structure, act, step, function, instruction, and/or the like used herein should be construed as critical or essential unless explicitly described as such. As used in the specification and the claims, the singular form of "a," "an," and "the" include plural referents unless the context clearly dictates otherwise. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

When a single device or article is described herein, it will be clear that more than one device/article (whether they cooperate) may be used in place of a single device/article. Similarly, where more than one device or article is described herein (whether they cooperate), it will be clear that a single device/article may be used in place of the more than one device or article or a different number of devices/articles may be used instead of the shown number of devices or articles. The functionality and/or the features of a device may be alternatively embodied by one or more other devices which are not explicitly described as having such functionality/features. Thus, other embodiments need not include the device itself.

In the following detailed description of the embodiments of the disclosure, reference is made to the accompanying drawings that form a part hereof, and [[in]] which are shown by way of illustrating specific embodiments in which the disclosure may be practiced. It should be understood, however, that it is not intended to limit the disclosure to the forms disclosed, but on the contrary, the disclosure is to cover all modifications, equivalents, and alternatives falling within the spirit and the scope of the disclosure. It is to be understood that other embodiments may be utilized and that changes may be made without departing from the scope of the present disclosure. The following description is, therefore, not to be taken in a limiting sense.

According to various embodiments, the present disclosure presents algorithmic approaches and new drive logic that utilizes motor control to ensure that the appropriate volume of fluid is delivered in the appropriate duration during an injection procedure or protocol when using a fluid injector system. The methods of the present disclosure compensate for volume variations due to compliance and the resulting under and over delivery of fluid volume over a given injection window to ensure optimized fluid delivery performance which meets flow rate, volume, and duration accuracy requirements.

Several types of fluid injector systems are available on the market, including piston driven syringe-based fluid injector systems, compression-based fluid injector systems, and fluid delivery using a peristaltic pump. Piston driven- and compression-based delivery technologies utilize movement of a piston or compressing surfaces at a constant or varying speed for a given duration or to a specific position to control the volume of fluid delivered and the flow profile. Peristaltic pump technologies utilize spinning rollers spinning at a given RPM with a known delivery volume per revolution or per minute to deliver a volume of fluid at a defined rate for a given time. Conventional injector technologies measure the volume of fluid delivered based on the programmed or set fluid flow rate(s) over the duration of the injection.

Figure 2:
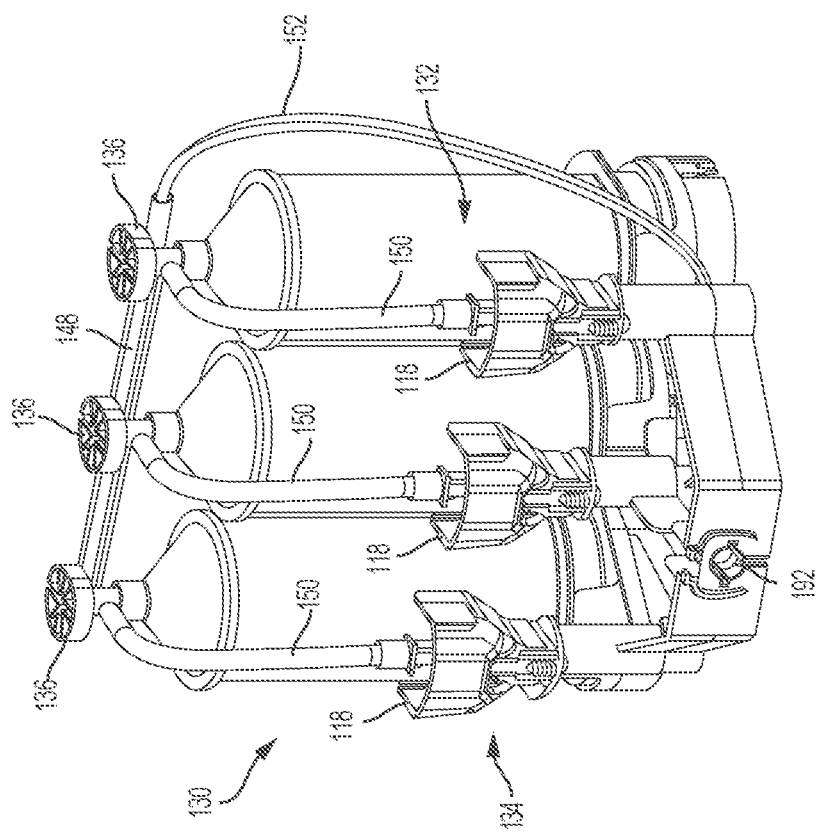
FIG. 2 is a perspective view of a multi-use disposable set for use with a fluid injector system of FIG. 1.

Referring to FIGS. 1-2, in which like reference characters refer to like parts throughout the several views thereof, one embodiment of the present disclosure is generally directed to a multi-fluid medical injector/injector system 100 (hereinafter "fluid injector system 100") which in certain embodiments may include a multi-use disposable set (MUDS) 130 configured for delivering fluid to a patient using a single-use disposable set (SUDS) connector and fluid path 190 (not shown in detail), and in various embodiments may include two, three, or more disposable fluid reservoirs or syringes, which may be disposed after one injection procedure or a specific number (multi-use) of injection procedures. The fluid injector system 100 may be a piston driven, syringe-based fluid delivery system and may include multiple components as described herein. Generally, fluid injector system 100 depicted in FIGS. 1-2 has a powered fluid injector or other administration device and a fluid delivery set intended to be associated with the powered fluid injector to deliver one or more fluids from one or more single- or multi-dose containers under pressure into a patient, as described herein. The various devices, components, and features of the fluid injector system 100 and the fluid delivery set associated therewith are described herein.

While the various examples of the methods and processes are shown with reference to the fluid injector system 100 having the MUDS 130 and the SUDS 190 configuration in FIGS. 1-2, the disclosure is not limited to such an injector system and may be utilized in other syringe based injector systems, such as but not limited to those described in U.S. Pat. Nos. 7,553,294; 7,563,249; 8,945,051; 9,173,995; 10,124,110; 10,507,319; 10,549,084; 10,583,256; and U.S. Application Publication No. 2018/0161496, the disclosures of each of which are incorporated herein in their entirety by this reference.

With reference to FIG. 1, the fluid injector system 100 according to one example includes an injector housing 102 that encloses the various mechanical drive components, electrical and power components necessary to drive the mechanical drive components, and control components, such as electronic memory, processors, and electronic control devices, used to control operation of reciprocally movable pistons (not shown) associated with the fluid injector system 100. Such pistons may be reciprocally operable via electro-mechanical drive components such as a ball screw shaft driven by a motor, a voice coil actuator, a rack-and-pinion gear drive, a linear motor, servo motor, stepper motor, and the like.

Fluid injector system 100 may include at least one bulk fluid connector 118 for connection with at least one bulk fluid source 120. In some examples, a plurality of bulk fluid connectors 118 may be provided. For example, as shown in the fluid injector embodiment in FIG. 1, three bulk fluid connectors 118 may be provided in a side-by-side or other arrangement. In some examples, the at least one bulk fluid connector 118 may include a spike configured for removably connecting to the at least one bulk fluid source 120, such as a vial, a bottle, or a bag. The at least one bulk fluid connector 118 may be formed on or part of the MUDS 130 (shown in FIG. 2). The at least one bulk fluid source 120 may be configured for receiving a medical fluid, such as saline, Ringer's lactate, an imaging contrast medium solution, or other medical fluid, for delivery to the patient by the fluid injector system 100.

With reference to FIG. 2, the MUDS 130 may be configured for removable connection to the fluid injector system 100 for delivering one or more fluids from the one or more bulk fluid sources 120 to the patient. Examples and features of embodiments of the MUDS 130 are further described in U.S. Pat. No. 10,507,319 and is operated with the SUDS 190 described in U.S. Pat. No. 10,549,084. The MUDS 130 may include one or more fluid reservoirs, such as one or more syringes 132. As used herein, the term "fluid reservoir" means any container capable of taking in and delivering a fluid, for example during a fluid injection procedure including, for example a syringe, a rolling diaphragm, a pump, a compressible bag, and the like. Fluid reservoirs may include the interior volume of at least a portion of a fluid pathway, such as one or more manifold or tubing lengths, that are in fluid communication with the interior of the fluid reservoir, including fluid pathway portions that remain in fluid communication with the fluid reservoir after the system is closed or fluidly isolated from the remainder of the fluid pathway with the closed system. The number of fluid reservoirs may correspond to the number of bulk fluid sources 120. For example, with reference to FIG. 2, the MUDS 130 may have three syringes 132 in a side-by-side arrangement where each syringe 132 is fluidly connectable to the three corresponding bulk fluid sources 120. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118 and fluid line 150. In some examples, the bulk fluid connector 118 may be provided directly on the MUDS 130.

With continued reference to FIGS. 1 and 2, the MUDS 130 may include one or more valves 136, such as stopcock valves, for controlling which medical fluid or combinations of medical fluids are withdrawn from the multi-dose bulk fluid source 120 (see FIG. 1) into the fluid reservoirs 132 and/or are delivered to a patient from each fluid reservoir 132 via manifold 148. In some examples, the one or more valves 136 may be provided on a distal end of the plurality of syringes 132 or on a manifold 148. The manifold 148 may be in selectable fluid communication via valves 136 with the interior volume of the syringes 132. The interior volume of the syringes 132 may be in selectable fluid communication via valves 136 with a first end of the MUDS fluid path 134 that connects each syringe 132 to the corresponding bulk fluid source 120. The opposing second end of the MUDS fluid path 134 may be connected to the respective bulk fluid connector 118. Depending on the position of the one or more valves 136, fluid may be drawn into the interior volume of the one or more syringes 132 or it may be delivered from the interior volume of the one or more syringes 132. In a first filling position, the one or more valves 136 are oriented such that fluid flows from the bulk fluid source 120 into the desired syringe 132 through a fluid inlet line 150. During the filling procedure, the one or more valves 136 are positioned such that fluid flow through one or more fluid outlet lines 152 and/or manifold 148 is blocked. In a second delivery position, fluid from one or more syringes 132 is delivered to manifold 148 through the syringe valve outlet ports. During the delivery procedure, the one or more valves 136 are positioned such that fluid flow through one or more fluid inlet lines 150 is blocked. In a third position, the one or more valves 136 are oriented such that fluid flow through the one or more fluid inlet lines 150 and the one or more fluid outlet lines 152 or the manifold 148 is blocked. Thus, in the third position, each of the one or more valves 136 isolates the corresponding syringe 132 and prevents fluid flow into and out of the interior volume of the corresponding syringe 132, thus defining a closed system. The one or more valves 136 and/or fluid outlet lines 152 may be integrated into or in fluid communication via the manifold 148. The one or more valves 136 may be selectively positioned to the first, second, and third position by manual or automatic handling.

With continued reference to FIGS. 1 and 2, according to some non-limiting embodiments, the fluid injector system 100 may have a connection port 192 that is configured to form a releasable fluid connection with at least a portion of the SUDS. In some examples, the connection port 192 may be formed on the MUDS 130. Desirably, the connection between the SUDS and the connection port 192 is a releasable connection to allow the SUDS to be selectively connected to and disconnected from the connection port 192. In some examples, the SUDS may be disconnected from the connection port 192 and disposed after each fluid delivery procedure, and a new SUDS may be connected to the connection port 192 for a subsequent fluid delivery procedure. The SUDS may be used to deliver one or more medical fluids to a patient by a SUDS fluid line having a distal end that may be selectively disconnected from the body of the SUDS and connected to a patient catheter.

Referring again to FIG. 1, the fluid injector system 100 may include one or more user interfaces 124, such as a graphical user interface (GUI) display. The user interface 124 may display information pertinent to a fluid injection procedure involving the fluid injector system 100, such as injection status or progress, current flow rate, fluid pressure, and volume remaining in the at least one bulk fluid source 120 connected to the fluid injector system 100 and may be a touch screen GUI that allows an operator to input commands and/or data for operation of the fluid injector system 100. Additionally, the fluid injector system 100 and/or user interface 124 may include at least one control button 126 for tactile operation by an operator. The at least one control button 126 may be a graphical part of the user interface 124, such as a touch screen, and/or may be located on a surface of the fluid injector system 100.

Figure 3:
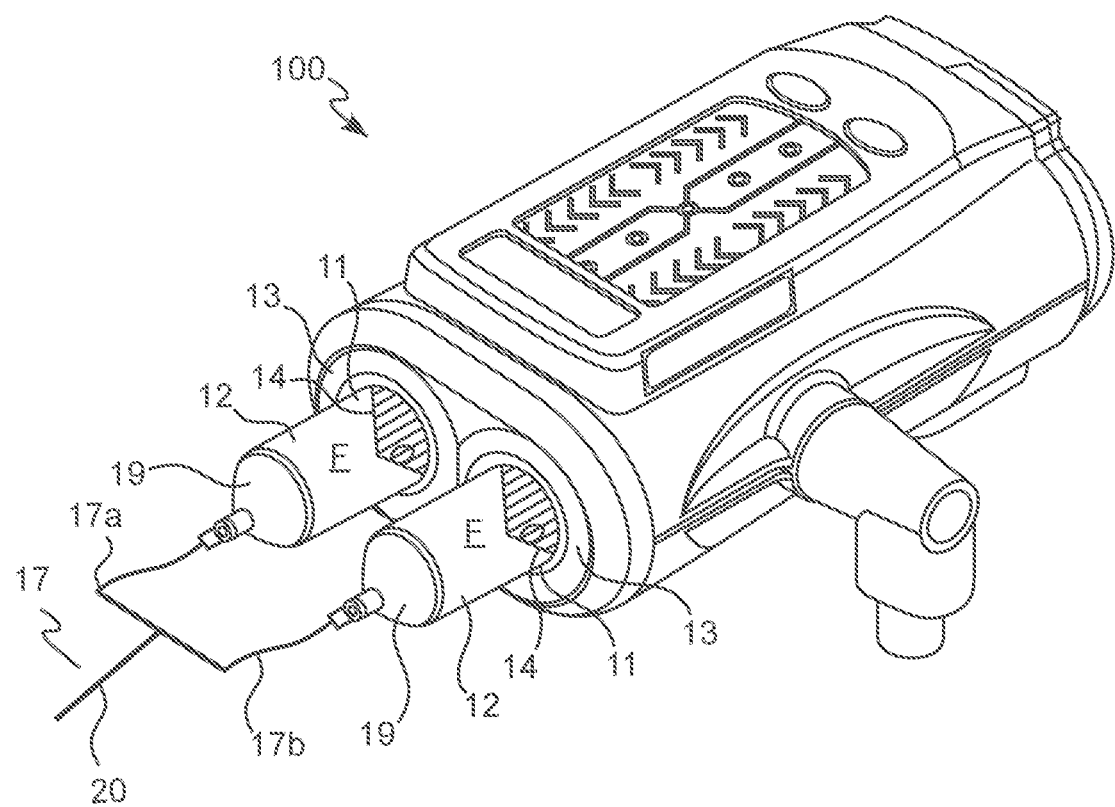
FIG. 3 is a perspective view of a fluid injector system according to another example of the present disclosure.

While FIGS. 1-2 illustrate one example of a fluid injector system 100, it is to be understood that the present disclosure is not limited to any particular type or variety of the fluid injector system 100. Referring now to FIG. 3, another non-limiting example of a fluid injector system 100 according to the present disclosure includes at least one fluid reservoir, such as a syringe 12, at least one piston (not pictured) connectable to at least one plunger 14, and a fluid control module (not pictured). The at least one syringe 12 is generally adapted to interface with at least one component of the system, such as a syringe port 13. The fluid injector system 100 is configured to releasably receive the at least one syringe 12, which is to be filled with at least one fluid F, as described herein. The system may be a multi-syringe injector, wherein several syringes may be oriented side-by-side or another spatial relationship which are separately actuated by respective pistons associated with the injector.

Figure 4:
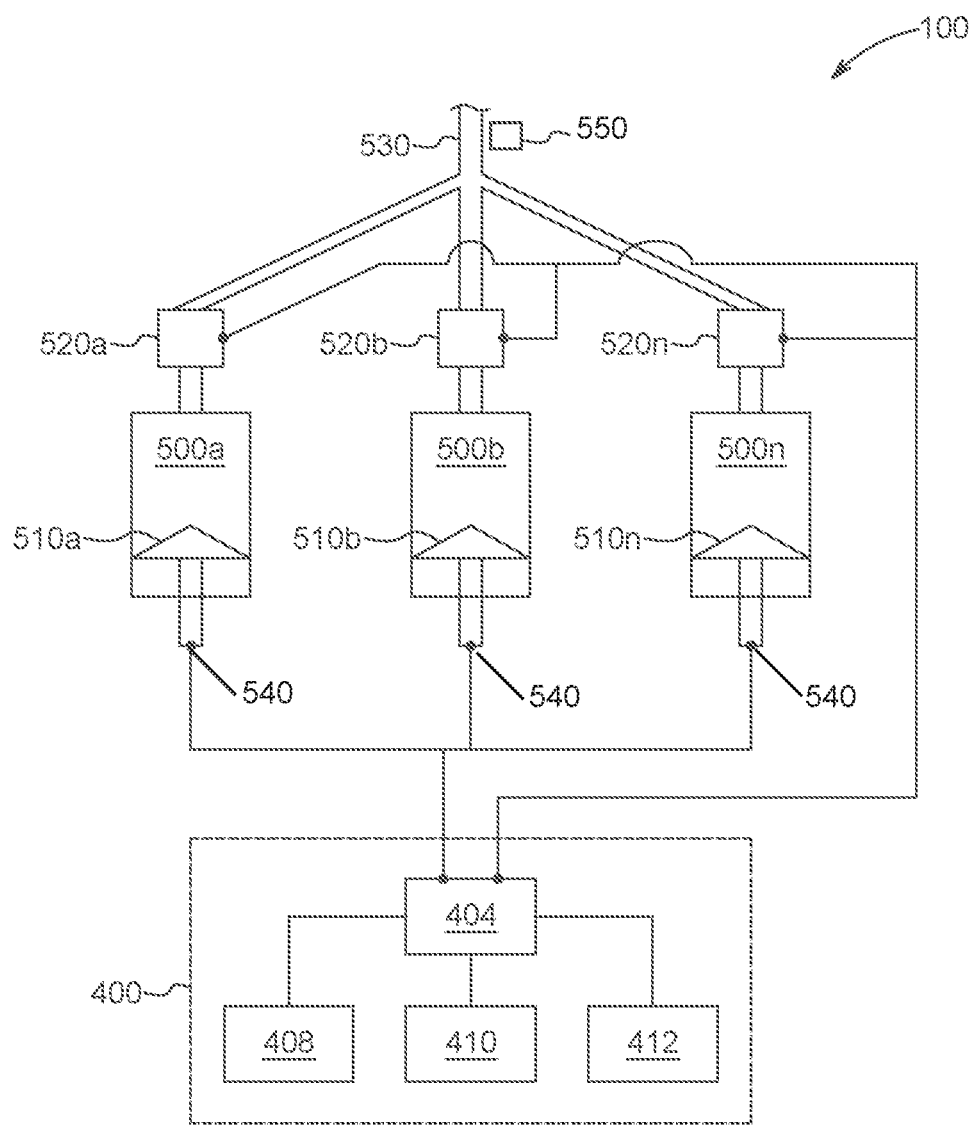
FIG. 4 is a schematic view of an electronic control system of a fluid injector system in accordance with examples of the present disclosure.

With continued reference to FIG. 3, the injector system 100 may be used during a medical procedure to inject the at least one medical fluid F into the vasculature system of a patient by driving a plunger 14 of at least one syringe 12 with a drive member, such as the at least one piston 103 (see FIG. 4). The at least one piston may be reciprocally operable upon at least a portion of the at least one syringe, such as the plunger 14. Upon engagement, the at least one piston may move the plunger 14 toward the distal end 19 of the at least one syringe, as well as retracting the plunger 14 toward the proximal end 11 of the at least one syringe 12. Non-limiting examples of fluid injector of FIG. 4 are described in U.S. Pat. No. 7,540,856.

A tubing set 17 (e.g., first and second fluid conduits 17a and 17b, and common fluid conduit 20) may be in fluid communication with an outlet port of each syringe 12 to place each syringe in fluid communication with a catheter for delivering the fluid F from each syringe 12 to the catheter (not shown) in a patient at a vascular access site. The first and second fluid conduits 17a and 17b may be connected to the common fluid conduit 20 by any suitable mechanism known in the art. The fluid injector system 100 shown in FIG. 3 is an open system due to the lack of valves capable of isolating the syringes 12 from one another and from at least a portion of the tubing set 17. However, it is to be understood that valves, similar to the valves 136 described herein, may be added distally of the syringes 12 to convert the fluid injector system 100 of FIG. 3 to a closed system.

Referring now to FIG. 4, fluid injector systems 100 in accordance with the present disclosure may be associated with and controlled by an electronic control device 400 configured to execute one or more injector protocols including, for example, the fluid filling, priming, and delivery operations. In some examples, the electronic control device 400 may control the operation of various valves, stopcocks, piston members, and other elements to affect a desired gas/air removal, fluid filling, and/or fluid delivery procedure. The control device 400 may be integrated into the fluid injector system 100, and/or may be separated from but in communication with the fluid injector system 100. The electronic control device 400 may include at least one processor 404, memory 408, an input component 410, and an output component 412. The electronic control device further may include a bus that permits communication among the components of the electronic control device 400. The at least one processor 404 may be implemented in hardware, firmware, or a combination of hardware and software. For example, processor 404 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 408 may include a hard disk (e.g., a magnetic disk, an optical disk, a magneto-optic disk, a solid-state disk, etc.) and/or another type of computer-readable medium. The input component 410 may include a component that permits the electronic control device 400 to receive information, such as via user input (e.g., the user interface 124). The output component 412 may include a component that provides output information from the electronic control device 400 (e.g., the user interface 124).

The electronic control device 400 may be programmed or configured to perform one or more processes and/or methods based on the at least one processor 404 executing software instructions stored by a computer-readable medium, such as memory 408. When executed, software instructions stored in memory 408 may cause the at least one processor 404 to perform one or more processes and/or methods described herein.

The number and arrangement of components of the electronic control device 400 shown in FIG. 4 are provided as an example. In some non-limiting embodiments, the electronic control device 400 may include additional components, fewer components, different components, or differently arranged components than those shown in FIG. 4. Additionally or alternatively, a set of components (e.g., one or more components) of the electronic control device 400 may perform one or more functions described as being performed by another set of components of the electronic control device 400.

With continued reference to FIG. 4, the electronic control device 400, more particularly the at least one processor 404, may be in operative communication with one or more components of the fluid injector system 100 to control an operation of the fluid injector system 100. The electronic control device 400 may be in operative communication with one or more drive components 510a, 510b, 510n respectively associated with one or more fluid reservoirs 500a, 500b, 500n of the fluid injector system 100 to control filling of fluid and delivery of fluid from the fluid reservoirs 500a, 500b, 500n. More particularly, each of the one or more drive components 510a, 510b, 510n may be associated with one of the fluid reservoirs 500a, 500b, 500n such that fluid contained in each of the fluid reservoirs 500a, 500b, 500n may be selectively delivered via actuation of the associated drive component 510a, 510b, 510n. The fluid reservoirs 500a, 500b, 500n may be, or may correspond to, the syringes 132 of the fluid injector system 100 of FIGS. 1-2 and/or the syringes 12 of the fluid injector system 100 of FIG. 3, as described herein. The one or more drive components 510a, 510b, 510n may be, or may correspond to, the pistons (not pictured) of the fluid injector systems 100 of FIGS. 1-3. The one or more fluid reservoirs 500a, 500b, 500n may be in fluid communication with a fluid conduit 530, such as a SUDS 190 or tubing set 17 for delivering fluid to a catheter or other component connected to a patient.

In certain examples of a closed fluid injector system 100 (e.g., the fluid injector system 100 of FIGS. 1 and 2), the electronic control device 400 further may be in operative communication with one or more valves 520a, 520b, 520n in order to rotate or otherwise actuate the valves 520a, 520b, 520n to direct flow into or out of and/or isolate flow from one or more of the fluid reservoirs 500a, 500b, 500n to the fluid conduit 530. The valves 520a, 520b, 520n may be, or may correspond to, the valves 136 described herein in FIG. 2.

In certain examples, at least one processor 404 may be programmed or configured to execute a fluid injection protocol (i.e., a fluid delivery procedure) during which at least one fluid is delivered to a patient. The fluid injection protocol may include a programmed flow rate, a desired volume of fluid to be delivered, and a type of fluid or a combination of two or more fluids to be delivered. Each fluid injection protocol may have one or more phases, with each phase having predetermined fluid flow, volume, and fluid type settings.

During a fluid injection procedure, a load is applied to the system by way of, e.g., one or more drive components 510a, 510b, 510n to deliver the fluid from one or more fluid reservoirs (i.e., fluid reservoirs 500a, 500b, 500n) to the patient via an administration line/fluid path set. The resulting change in fluid pressure within each of the fluid reservoirs (i.e., fluid reservoirs 500a, 500b, 500n) may cause the system to store some elastic energy in the form of increased internal volume (i.e., swelling) of the fluid reservoirs 500a, 500b, 500n, and/or elastic mechanical deflection of, e.g., the plungers coupled to each drive component, etc. and mechanical slack associated with injector components. This pressure-dependent increase in volume is known as the compliance volume of the system. Based on known characteristics of each fluid reservoir 500a, 500b, 500n and the fluid injector system 100 as a whole, a measured change of fluid pressure within the system allows for a corresponding change in compliance volume to be calculated. In one embodiment, compliance volume may be determined via a global equation executed by the at least one processor 404 using information regarding changes in fluid pressure, fluid flow rate, etc. In another embodiment, the compliance volume may be determined through the use of one or more sensors capable of measuring, e.g., expansion, deflection, etc. of the various components of the system. In still another embodiment, the compliance volume of a specific component (e.g., a certain size/model of fluid reservoir) may be predetermined, and the component may include a scannable bar code or other indicator that provides the compliance volume characteristics of the component under various pressure and flow rate conditions. It is to be understood that other methods of determining compliance volume are also possible.

During an injection procedure, fluid flow increase out of the injector is typically accompanied by a pressure increase within the fluid reservoir or pump associated with the injector. However, increases in pressure over a period of time may result in further increase in pressure of the system beyond the programmed increase, for example, due to mechanical deflection, or intrinsic fluid dynamics of mixing fluids with differing densities. For example, if the pressure of the fluid delivery is increased by 100 psi over a time period of 1 second, then the fluid flow rate must be increased to compensate for the increase in pressure.

System compliance may cause gradients in pressure, which cause deviations in the actual flow rate from a programmed flow rate. Similarly, gradients in fluid flow rates can result in gradients in pressures within a fluid injection system. However, if the pressure does not significantly change during an injection, then the fluid flow rate may be considered to be substantially constant. This is possible if the various effects from fluid injector features, such as effects resulting from position-based changes in system compliance or the effects resulting from creep over time, are ignored. Under ideal conditions, if the pressure reaches steady state pressure instantaneously, there should be a square wave for the fluid flow rate. However, system compliance in conventional fluid injection systems, for example in the form of volumetric swelling of fluid delivery components such as fluid reservoirs, and tubing; or volumetric increases due to taking up mechanical slack under pressurized delivery conditions, may result in fluid flow inaccuracies before the injector reaches a steady state pressure profile.

Figure 5:
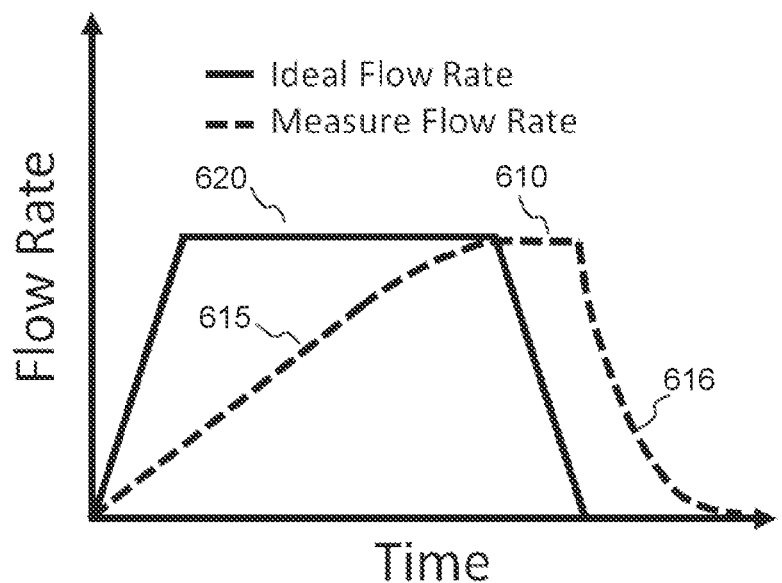
FIG. 5 illustrates a typical injection profile using conventional injector technologies compared with an injection profile utilizing an embodiment of the pressure-based servo control of the present disclosure.

With reference to FIG. 5, a fluid flow profile 610 is shown for a fluid injection protocol where compliance volume affects the volumetric accuracy of the fluid delivered to the patient (dotted line) in comparison to a fluid flow profile for an injection protocol where pressure reaches steady state pressure near instantaneously (solid line). As can be seen in FIG. 5, inaccuracies in fluid volume delivery are illustrated by tailing at the beginning 615 (during compliance volume uptake) and at the end 616 (during compliance volume release) of a measured flow rate curve 610 of an exemplary fluid injection procedure. Broadening of the bolus shape over time generally results from compliance volume effects. On the other hand, a programmed flow rate curve 620 preferably has a near instantaneous rise to the programmed flow rate, which is maintained for the duration of the injection procedure, followed by a near instantaneous drop to zero flow rate. The substantially square profile of the programmed flow rate curve 620 desirably rises to a steady state pressure substantially instantaneously and shows no or only minimal tailing at the beginning and at the end of the fluid injection procedure.

Non-limiting embodiments of the present disclosure are directed to systems, devices, products, apparatus, and/or methods for improved and accurate fluid delivery profiles by instituting a pressure-based control of fluid rate by controlling one or more drive components (e.g., one or more drive components 510a, 510b, 510n) using the electronic control device 400, such as the at least one processor 404. According to various embodiments, the flow rate commanded by the one or more drive components 510a, 510b, 510n is based on a previously measured change in pressure over a short time interval and the flow rate is adjusted by an algorithmic analysis of the change in pressure compared to the expected change in pressure. Using a real-time feedback loop over the duration of the fluid delivery, an accurate relationship between changes in pressure of the fluid and true fluid flow rates can be utilized to make adjustments to the next measured fluid flow rate, correcting for either over or under delivery of fluid over the short time interval, so that the resulting flow rate profile has a more square flow profile with minimized tailing (similar to 620 in FIG. 5).

Figure 9A:
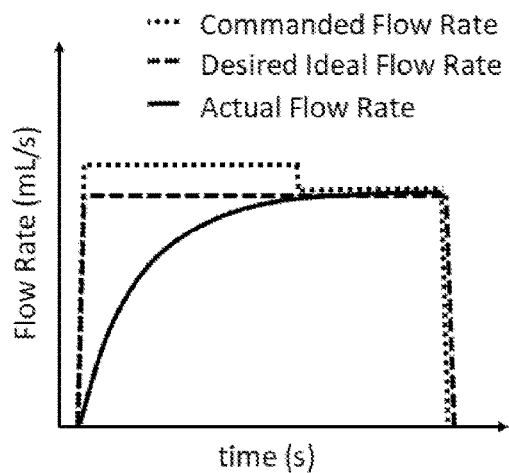
FIG. 9A is a graph showing a change in flow rate as a function of time for a sub-optimal bounding function in accordance with a first example.
Figure 9B:
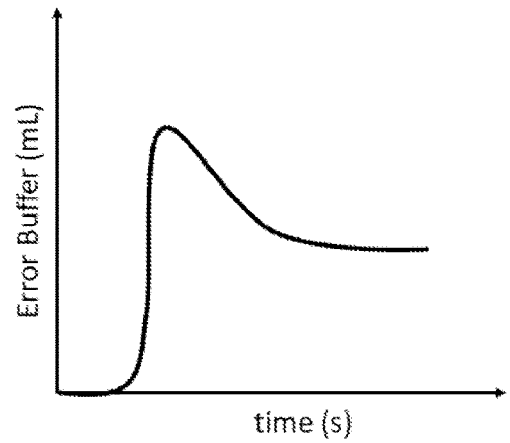
FIG. 9B is a graph of an error buffer (in ml) as a function of time for the sub-optimal bounding function shown in FIG. 9A.
Figure 10A:
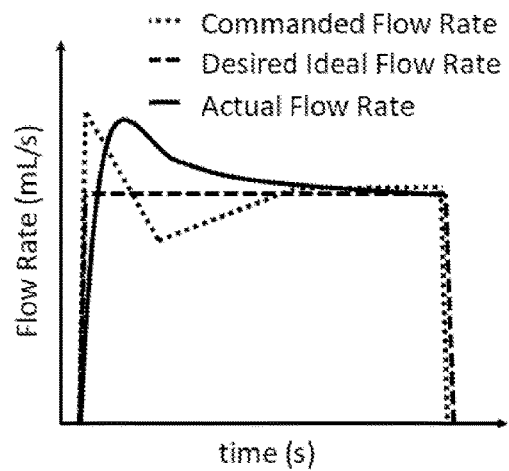
FIG. 10A is a graph showing a change in flow rate as a function of time for a sub-optimal bounding function in accordance with a second example.
Figure 10B:
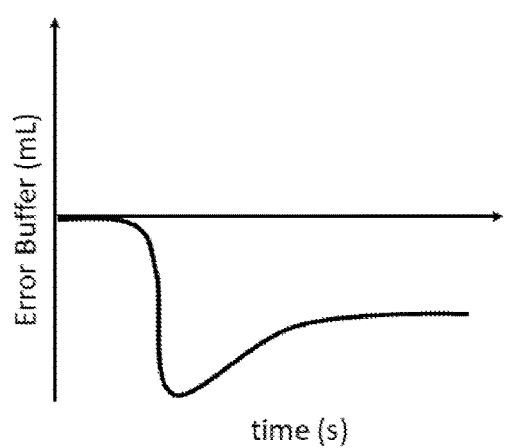
FIG. 10B is a graph of an error buffer (in ml) as a function of time for the sub-optimal bounding function shown in FIG. 10A.

According to various embodiments, tuning the system response may be important for the implementation of the method. If the system response is too slow, fluid may be delivered at an undesired flow rate for a longer duration. For example, with reference to FIGS. 9A, 10A, 11A, and 12A, the solid lines indicating an actual flow rate deviate significantly from desired flow rates (dashed lines) or commanded flow rates (dotted lines). The associated error buffer (expressed in mL) shown in FIGS. 9B, 10B, 11B, and 12B indicates an over- or under-delivery of fluid as a function of time for systems with sub-optimal or unacceptable fluid delivery profiles. In instances where the pressure is increasing, this means that the actual flow rate is below the desired rate (FIGS. 9A-9B) and when pressure is decreasing the actual flow rate will be higher than desired (FIGS. 10A-10B). For injections of short duration or low volume, an overly dampened response, such as that exemplified in FIGS. 11A-11B, is unacceptable. Conversely, if the initial response is too aggressive or the system is stiff relative to the established bounds, the system may overshoot the desired flow rate and will deliver at a higher flow rate than desired for some duration and require additional time to recover and approach the desired rate (FIGS. 10A-10B). If the bounding function is hyper-responsive for a given system, the method may introduce undesired oscillations in flow rate (FIGS. 12A-12B).

Figures 13A, 13B:
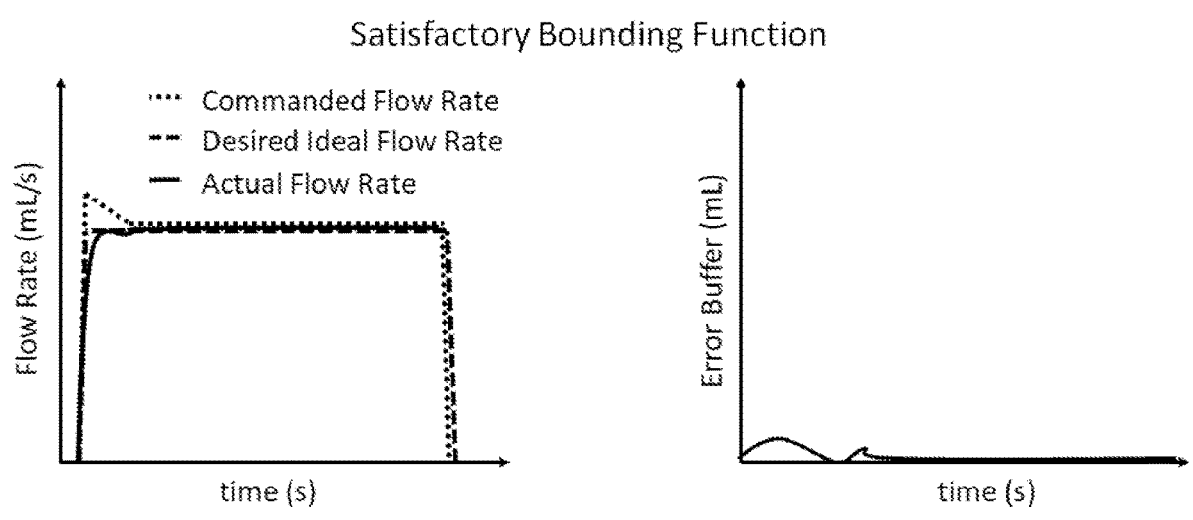
FIG. 13A is a graph showing a change in flow rate as a function of time for a satisfactory bounding function in accordance with some non-limiting embodiments of the present disclosure.
FIG. 13B is a graph of an error buffer (in ml) as a function of time for the satisfactory bounding function shown in FIG. 13A.

Considering the scenarios shown in FIGS. 9A-12B, in order to produce the desired injector performance, the present disclosure tunes the system response to pressure such that flow rate adjustments are balanced with the pressure response of the system, which is dictated by the stiffness of the system including fluid reservoirs, tubing or other fluid path components, injector components, and the fluid being delivered. To avoid slow or reinforcing feedback, in some non-limiting embodiments of the present disclosure, the systems and methods described herein scale pressure measurements and convert the input to a flow rate in order to provide a direct comparator for the desired flow rate. In addition, the measurement interval is selected to provide the desired responsiveness, while a maximum allowable deviation in pressure for a given time interval prevents a hyper-sensitive response and provides sufficient time for the physical system to act. Incorporation of the maximum allowable deviation with the error buffer allows for relatively large deviations in flow rate achieved without introducing undesired fluctuations or straining system components. With reference to FIG. 13A, the solid line indicating an actual flow rate substantially matches the desired flow rates (dashed line) or commanded flow rate (dotted line). The associated error buffer (expressed in mL) shown in FIG. 13B is tuned to minimize over- or under-delivery of fluid as a function of time.

According to various embodiments, changes in pressure may be measured by determining, for example, a force applied by the one or more drive components 510a, 510b, 510n. In some embodiments, a force sensor 540 may be associated with each of the one or more drive components 510*a*, 510*b*, 510*n* and may be configured for measuring a force exerted by the one or more drive components 510*a*, 510*b*, 510*n*. In some embodiments, pressure may be measured using the one or more drive components 510*a*, 510*b*, 510*n*. For example, pressure may be measured by measuring a current of a motor of the one or more drive components 510*a*, 510*b*, 510*n* and correlating the current measurement to a pressure. In this manner, the one or more drive components 510*a*, 510*b*, 510*n* function as the sensor. The pressure measurement obtained by the force sensor 540 and/or the current measurement of the one or more drive components 510*a*, 510*b*, 510*n* is an estimated pressure measurement because it is based on an indirect measurement. According to further embodiments, changes in pressure may be measured by other methods, such as one or more pressure sensors 550 configured for measuring an actual fluid pressure in a fluid reservoir and/or a fluid path set (such as one or more of fluid reservoirs 500*a*, 500*b*, 500*n* and/or the fluid conduit 530).

Instead of determining the fluid flow rate by a programmed or set flow rate over the duration of the entire fluid injection procedure, a programmed flow rate profile is achieved by measuring an actual flow rate during a plurality of discrete time intervals during the fluid injection procedure. Actual flow rate is determined by measuring differences in fluid pressure during each time interval, and the actual flow rate for each time interval is then compared to the desired fluid flow rate. Pressure is adjusted dynamically after each time interval to compensate for over or under delivery of fluid volume in a subsequent time interval(s).

In some embodiments, the electronic control device 400 may be configured to perform flow rate control by controlling operation of the one or more drive components 510*a*, 510*b*, 510*n* based on pressure measurements determined by at least one sensor, such as the force sensor 540 and/or the pressure sensor 550. In further embodiments, the electronic control device 400 may be configured to perform pressure control by controlling operation of the one or more drive components 510*a*, 510*b*, 510*n* based on pressure measurements determined by at least one sensor, such as the force sensor 540 and/or the pressure sensor 550. For example, the electronic control device 400, more particularly the at least one processor 404, may be configured for determining an actual flow rate/pressure during a time interval of the fluid delivery procedure based on a change in pressure measured by the at least one sensor (such as the force sensor 540, the pressure sensor 550, and/or the current of a motor of the one or more drive components 510*a*, 510*b*, 510*n*) over the time interval during execution of the fluid delivery procedure. The time interval can be any fraction of the run time of the fluid delivery procedure. In some embodiments, the time interval can be 1 millisecond to 5000 milliseconds. In other words, the actual flow rate/pressure during the time interval can be determined by taking pressure measurements at a beginning (first pressure measurement) and an end (second pressure measurement) of the time interval.

As discussed herein, the pressure may be measured by the force required to move a servo control motor that operates a piston of a fluid injection device or a servo control motor that operates a peristaltic pump injection device. According to certain embodiments, the force may be measured by the current necessary for the motor to move the drive component. A difference between the second pressure measurement and the first pressure measurement is the change in pressure that occurs during the time interval.

The calculated change in pressure may be scaled using one or more scaling factors to account for fluid over-delivery/under-delivery caused by, for example, uptake of or release of compliance volume of fluid in the injector system. Such scaling factor(s) may be unique to the fluid injector system and/or the fluid injection procedure being performed. The scaling factor(s) may vary based on the characteristics of at least one of the one or more drive components 510*a*, 510*b*, 510*n*, the one or more fluid reservoirs 500*a*, 500*b*, 500*n*, the fluid contained in the one or more fluid reservoirs 500*a*, 500*b*, 500*n*, the fluid conduit 530, and the pressure required to deliver the fluid during the fluid delivery procedure. The scaling factor(s) may be expressed as an algorithmic equation, such as a linear algorithmic equation. In some embodiments, the algorithmic equation may include non-linear functions, such as an exponential relationship between the change in pressure and the scaled pressure value.

The electronic control device 400, more particularly the at least one processor 404, may be further configured to determine an actual flow rate of fluid over the time interval during execution of the fluid delivery procedure. For example, the actual flow rate may be expressed as a function of the scaled change in pressure over the duration of the time interval. The electronic control device 400, more particularly the at least one processor 404, may be further configured to determine a change in flow rate based on an absolute value of a difference between the actual flow rate and the programmed flow rate. The electronic control device 400 may determine the change in flow rate at each time interval.

In some embodiments, a maximum allowable deviation or change in flow rate between the actual flow rate and the programmed flow rate may also be stored in the memory 408 of the electronic control device 400. The maximum allowable deviation or change in flow rate represents the highest permissible difference between the actual flow rate and the programmed flow rate during each time interval of the fluid delivery procedure.

In some embodiments, a deviation or change in flow rate between the actual flow rate and the programmed flow rate may be limited by predetermined bounds. In various embodiments, the predetermined bounds may be a preset minimum and maximum threshold, a percentage of the programmed flow rate, a function based on one or more factors including the programmed flow rate, statistical limits based on standard deviation from the programmed flow rate, a moving average of the actual flow rate relative to the programmed flow rate, and any combination thereof.

The electronic control device 400, more particularly the at least one processor 404, may be further configured to compare the maximum allowable deviation or change in the flow rate to the change in flow rate between the actual flow rate and the programmed flow rate over the time interval. The result of this comparison is a flow rate correction that can be used to determine a new programmed flow rate for a subsequent time interval, as discussed herein. In this manner, the new programmed flow rate for the subsequent time interval may be adjusted to increase or decrease the programmed flow rate from the previous time interval in order to account for any under or over delivery of fluid during the previous time interval, respectively.

In some embodiments, the flow rate correction may be equal to the maximum allowable change in flow rate if the change in flow rate between the actual flow rate and the programmed flow rate is higher than the maximum allowable deviation or change. In further embodiments, the flow rate correction may be equal to the actual flow rate if the change in the flow rate between the actual flow rate and the programmed flow rate is less than or equal to the maximum allowable deviation or change. A difference between the change in flow rate and the maximum allowable deviation or change in flow rate may be stored in the memory 408 of the electronic control device 400 as a buffer deviation for use in determining a new flow rate correction in subsequent time intervals after the second time interval. In this manner, the error in the amount of fluid that is actually delivered during the fluid delivery procedure may be spread over multiple time intervals instead of being accounted for only in a subsequent time interval to the time interval in which the error was accumulated. For example, a fraction of the difference between the change in flow rate and the maximum allowable deviation or change in flow rate may be added to each of a plurality of time intervals after the time interval in which the error was accumulated. The flow rate correction for each subsequent time interval may be based on a difference between the maximum allowable deviation and the deviation of the actual flow rate from the programmed flow rate over each subsequent time interval, and a buffer deviation from a previous time interval.

The calculation of a new programmed flow rate can be repeated for each subsequent time interval, up to the last time interval of the fluid injection procedure. In this manner, the new programmed flow rate from a previous time interval is used as a programmed flow rate for the current time interval, and an updated programmed flow rate is calculated for the subsequent time interval.

According to various embodiments, an example of injector logic that may be programmed into the at least one processor 404 of the electronic control device 400 may include the following steps:

Initializing all variables to zero,

Setting a programmed flow rate (Fd) to be used during the specified time interval of the fluid injection procedure, Setting a maximum allowable change in flow rate (ΔFmax) as a maximum difference in flow between an actual flow rate and a programmed flow rate, Initiating the fluid delivery procedure by actuating at least one drive component, Measuring a first pressure (P1) at a start of the specified time interval using pressure/force sensor and/or motor current measurement, Measuring a second pressure (P2) at an end of the specified time interval using pressure/force sensor and/or motor current measurement, Determining the change in pressure (ΔP) over the specified time interval and adding any over-delivery (OD) from a previous time interval (ΔP=P2−P1+OD), Determining a scaled change in pressure (ΔPs) based on the calculated change in pressure (ΔP) and one or more scaling factors (ΔPs=A*ΔP+B, where A and B are constants that are unique to each injector system), Determining an actual flow rate (Fa) for the specified time interval based on a scaled change in pressure between the end (T2) and the beginning (T1) of the specified time interval (Fa=ΔPs/(T2−T1)), Determining a change in flow rate (ΔFr) based on an absolute value of a difference between the actual flow rate (Fa) and the programmed flow rate (Fd) (ΔFr=|Fa−Fd|), Comparing the change in flow rate (ΔFr) with maximum allowable change in flow rate (ΔFmax), If the change in flow rate (ΔFr) is greater than the maximum allowable change in flow rate (ΔFmax) (ΔFr>ΔFmax), any over delivery or under delivery is to be corrected for over more than one time interval, Setting the fluid flow rate correction (F*) to be equal to the maximum allowable change in flow rate (ΔFmax) (F*=ΔFmax), Storing the difference between the change in flow rate (ΔFr) and the maximum allowable change in flow rate (ΔFmax) in an over-delivery buffer (OD) to be added over one or more subsequent time interval(s), If the change in flow rate (ΔFr) is less than or equal to the maximum allowable change in flow rate (ΔFmax) (ΔFr<=ΔFmax), any over delivery or under delivery can be corrected for over the subsequent time interval, Setting the flow rate correction (F*) to be equal to the delta flow rate F*=ΔFr, Determining a new programmed flow rate (Fn) for the next time interval where the new rate is based on a combination of the desired flow (Fd) rate for the previous time interval and the flow rate correction (F*) (Fn=Fd+F*), and Repeating the process for the remaining time intervals in the fluid delivery procedure using the new flow rate (Fn) from each time interval as the programmed flow rate in a subsequent time interval.

According to further embodiments, an example of injector logic that may be programmed into the at least one processor 404 of the electronic control device 400 may include the following steps:

Initializing all variables to zero, including pressure values, time, pressure error, and position error, Setting a maximum change in a commanded position of the one or more drive components 510a, 510b, 510n (Δx_command_max) to the programmed flow rate (Fd). In certain embodiments, the programmed volume may be equal to the sum of the commanded changes in position and the volumetric component from measured pressure change. In specific embodiments, sum of all Δx_command (Δx_command_sum, as detailed herein) may not be set at the beginning of the protocol as the volumetric component from measured pressure change may not be known a priori, as the volumetric component may depend on the measured pressure during the injection, Measuring a current pressure (P_measured) and a current position (x_measured) at a first time (t=0), Setting a first timer equal to the duration of a number of iterations of the pressure control loop (Duration_1=N*Duration_2), Setting a second timer equal to a predetermined length of time (e.g., 10 μs) (Duration_2), Calculating a pressure error using equation where pressure error is a difference between the measured pressure and the predetermined pressure. Pressure error can be calculated as Pressure_error=P_set−P_measured; or Pressure_error=P_measured−P_set, The equation used depends on the final implementation of the controller (generally related to circuitry details), Calculating the change in the commanded position of the one or more drive components 510a, 510b, 510n as a function of the calculated pressure error using Equation 1:

$$\Delta x_{command} = K_{P1} * e_p + K_{I1} * \int_0^\tau e_p(t)dt + K_{D1} * \frac{de_p(t)}{dt} \quad \text{(Equation 1)}$$

where K_P1, K_I1, and K_D1, are gains to scale any of the value of pressure error, integral of pressure error, and derivative of pressure error, respectively. These "pressure gains" may be obtained by any number of theoretical and empirical methods. For example, the values for K_P1, K_I1, and K_D1 may be obtained using the Ziegler-Nichols method to generate a static pressure in a closed fluid container, such as a syringe, at a plurality of pressure over the programmed pressure range, If the commanded change of the one or more drive components 510a, 510b, 510n results is greater than the programmed flow rate (Fd), the commanded position change is set to the programmed flow rate (Fd), If the commanded position of the one or more drive components 510a, 510b, 510n results is less than 0, the commanded position is set to 0, Calculating the position error as a function of the measured position and the commanded position of the one or more drive components 510a, 510b, 510n using the following equations:

Position_error=x_measured−x_command; or

Position_error=−x_command−x_measured,

Calculating the current (or other motion command) delivered to a motor drive component as a function of Position_error, using Equation 2:

$$i = K_{P2} * e_X + K_{I2} * \int_0^T e_X(t)dt + K_{D2} * \frac{de_X(t)}{dt} \quad \text{(Equation 2)}$$

where K_P2, K_I2, K_D2, are gains to scale the value of position error, the integral of position error, and the derivative of position error, respectively, and i is the current (or other command). These "position gains" may be obtained by any number of theoretical and empirical methods, Starting the timers for Duration_1 and Duration_2, Actuating the calculated motor drive based on the calculated current command i, Measuring the new position (x_measured) at the end of Duration_2, Calculating the new position error by the previously utilized relationship, Calculating the new motor drive command i by the previously utilized relationship, Repeating the loop until Duration_1 expires (i.e., N times), Resetting the timers for Duration_1 and Duration_2, Measuring the new current pressure (P_measured), Calculating the new pressure error, Calculating the new change in commanded position of the one or more drive components 510a, 510b, 510n, Starting the timers for Duration_1 and Duration_2, and Repeating the loop of pressure and position control until the sum of all Δx_command (Δx_command_sum) and the volumetric component scaled from measured pressure change is equal to Vd. The function that describes the volumetric component is generally a nonlinear combination of scaled pressure (p) and scaled piston position (x). For example, according to an embodiment, the volumetric component is calculated by the following equation (3):

$$V\_c = A + B*p + C*x + D*p^2 + E*x^2 + F*p*x \quad \text{(Equation 3)}$$

where A through F are scaling factors, p is pressure, and x is piston position.

Figure 6:
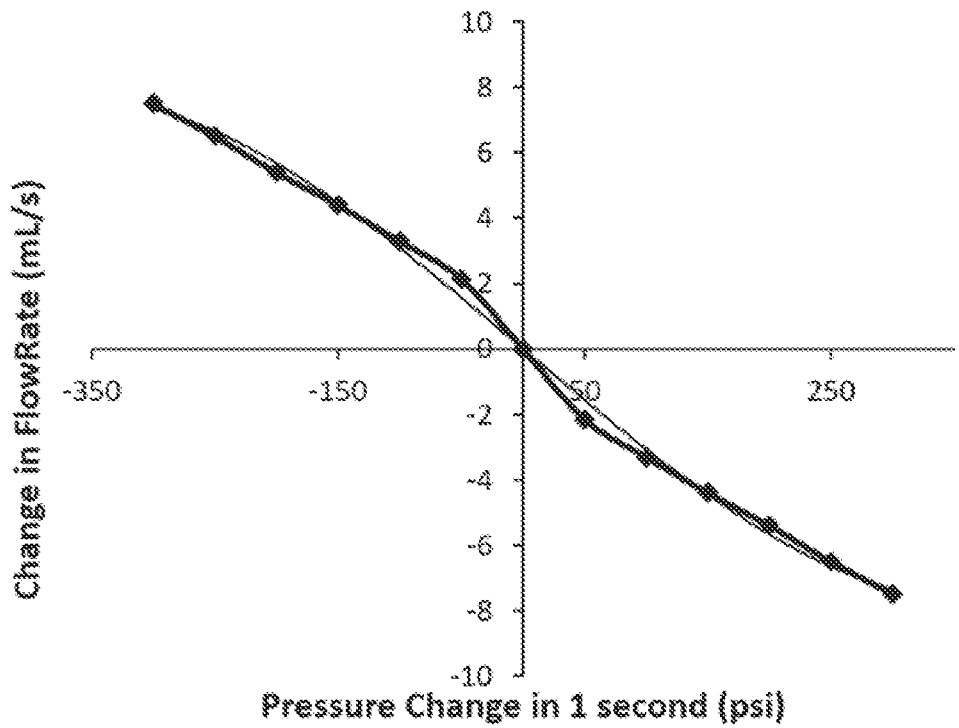
FIG. 6 is a graph showing a change in flow rate as a function of change in pressure over a predetermined time interval of a fluid injection protocol.

FIG. 6 illustrates a graphical relationship between the change in pressure versus the change in flow rate for one embodiment of an injector system using the injector logic described herein. For example, using the graph in FIG. 6, a change in flow rate (mL/s) can be determined for the fluid injector based on an observed or determined change in pressure over a time interval (1 sec according to the embodiment of FIG. 6).

Figure 7:
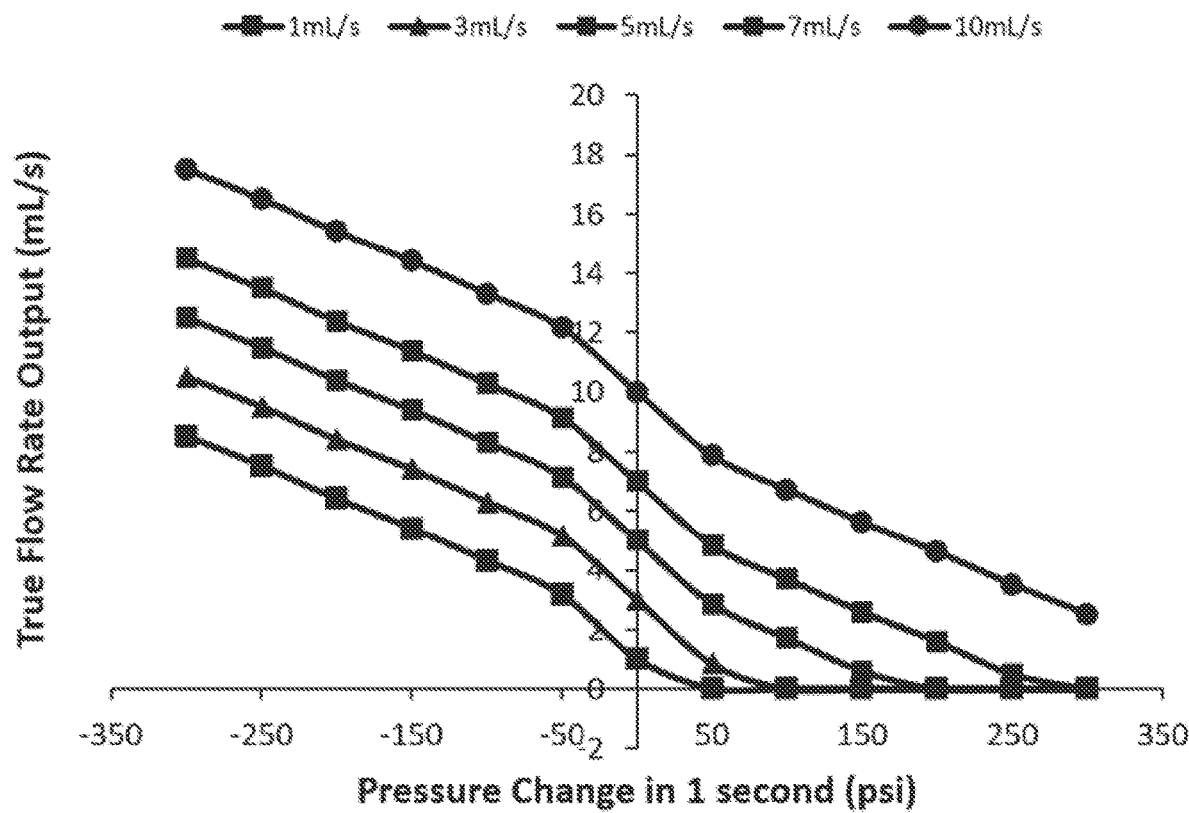
FIG. 7 is a graph showing a change in a plurality of actual flow rates as a function of changes in pressure over a predetermined time interval of a fluid injection protocol.

FIG. 7 illustrates a graphical relationship of the resulting transformation calculation of the actual flow rate for specific programmed flow rates for one embodiment of an injector system using the injector logic of the present disclosure. Using the plot in FIG. 7, a difference between the true flow rate output for the injector system is determined for an observed pressure change over a time interval (1 sec) for specific programmed fluid flow rates.

Figure 8:
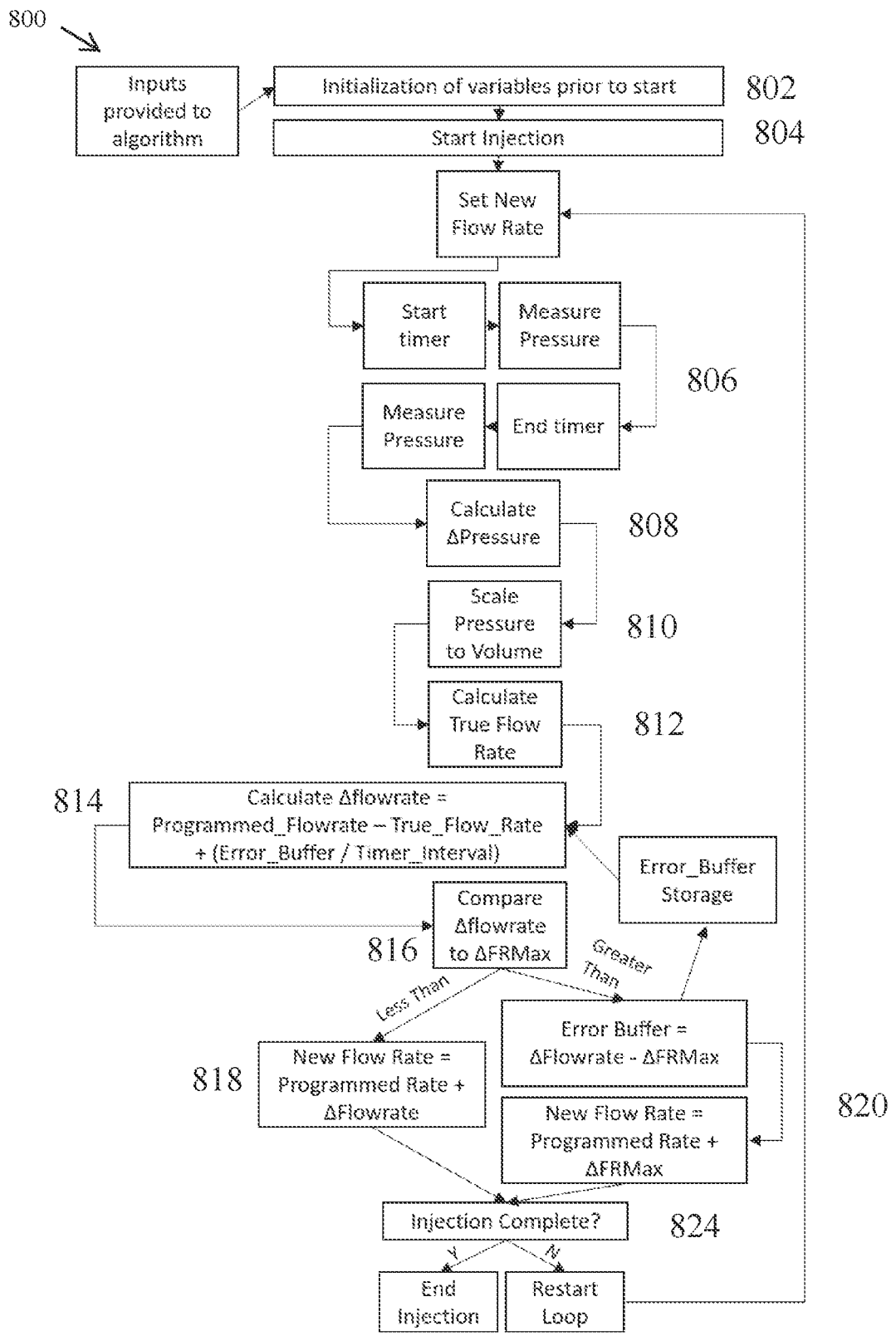
FIG. 8 is a representative flow chart of a flow control process in accordance with some non-limiting embodiments of the present disclosure.

Having described the structure of various fluid injector systems 100 and electronic control devices 400 configured for controlling operation of the various fluid injector systems 100, a method 800 for improved fluid delivery using real-time, pressure-based control of one or more drive components 510a, 510b, 510n of a fluid injector system 100 during a fluid injection procedure will now be described with reference to FIG. 8.

Prior to initiating a fluid delivery procedure at step 804, such as via actuation of one or more drive components 510a, 510b, 510n of fluid injector system 100 using the electronic control device 400, a programmed flow rate for a specified time interval of the fluid delivery procedure and a maximum allowable change in the flow rate during any time interval are set at step 802. For example, the programmed flow rate and the maximum allowable deviation or change in the flow rate may be stored in the memory 408 of the electronic control device 400.

During the initial time period and at step 806, a first pressure is measured at the start of the time period and a second pressure is measured at the end of the time period. As described herein, pressure may be measured using one or more force sensors 540 associated with the one or more drive components 510a, 510b, 510n and/or one or more pressure sensors 550 associated with one or more of fluid reservoirs 500a, 500b, 500n and/or fluid conduit 530.

At step 808, a change in pressure during the time interval is determined. A difference between the second pressure measurement and the first pressure measurement is the change in pressure that occurs during the time interval.

At step 810, a scaled change in pressure is determined using one or more scaling factors to account for fluid over-delivery/under-delivery caused by, for example, uptake of or release of compliance volume of fluid in the injector system. As described herein, the scaling factor(s) may vary based on the characteristics of at least one of the one or more drive components 510a, 510b, 510n, the one or more fluid reservoirs 500a, 500b, 500n, the fluid contained in the one or more fluid reservoirs 500a, 500b, 500n, the fluid conduit 530, and the pressure required to deliver the fluid during the fluid delivery procedure. In some embodiments, the scaled pressure may be determined by an algebraic equation, such as a linear or non-linear algebraic equation.

At step 812, an actual flow rate during the time interval is determined. The actual flow rate may be expressed as a function of the scaled change in pressure over the duration of the time interval.

At step 814, a change in flow rate between the actual flow rate and the programmed flow rate is determined. The change in flow rate may be expressed as an absolute value of the difference between the actual flow rate and the programmed flow rate.

At step 816, a flow correction is determined which may be used for correcting a programmed flow rate in a subsequent time interval. The flow correction is based on a comparison of the change in the flow rate determined in step 814 and the stored maximum allowable change in the flow rate (step 802). If the change in the flow rate determined in step 814 is greater than the maximum allowable change in flow rate set in step 802, then any over-delivery or under-delivery in fluid is to be corrected for over more than one time interval. In this manner, the fluid flow rate correction is set to be equal to the maximum allowable change in flow rate (step 818) and the difference between the change in the flow rate and the maximum allowable change in flow rate is stored in a buffer to be added over one or more subsequent time interval(s). On the other hand, if the change in the flow rate determined in step 814 is less than or equal to the maximum allowable change in flow rate set in step 802, then any over-delivery or under-delivery in fluid is to be corrected for the subsequent time interval by setting the flow rate correction to be equal to the actual flow rate (step 820).

At step 822, a new programmed flow rate for the subsequent time interval is determined, where the new programmed flow rate is based on a combination of the programmed flow rate for the current time interval (step 802) and the flow rate correction determined in steps 816-820.

At step 824, the process of steps 802-822 is repeated for the remaining time intervals in the fluid delivery procedure using the new programmed flow rate from each time interval as the programmed flow rate in a subsequent time interval.

In accordance with some non-limiting embodiments, a second method 900 for improved fluid delivery using real-time, pressure-based control of one or more drive components 510a, 510b, 510n of a fluid injector system 100 during a fluid injection procedure will now be described with reference to FIG. 16. The method 900 may be implemented using a pressure control system shown in FIG. 15.

Figure 15:
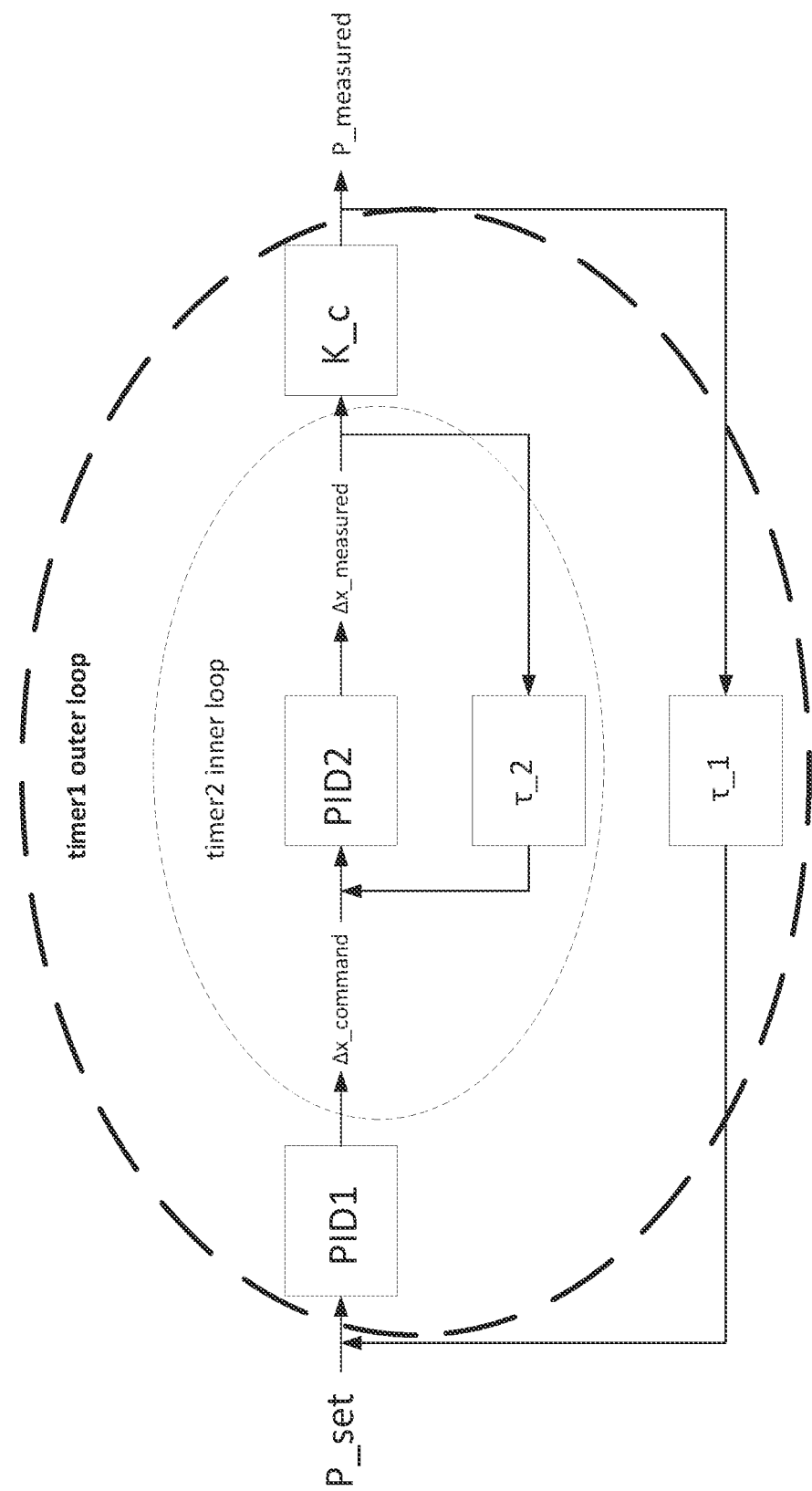
FIG. 15 is a schematic representation of a pressure control system in accordance with some non-limiting embodiments of the present disclosure.
Figure 16:
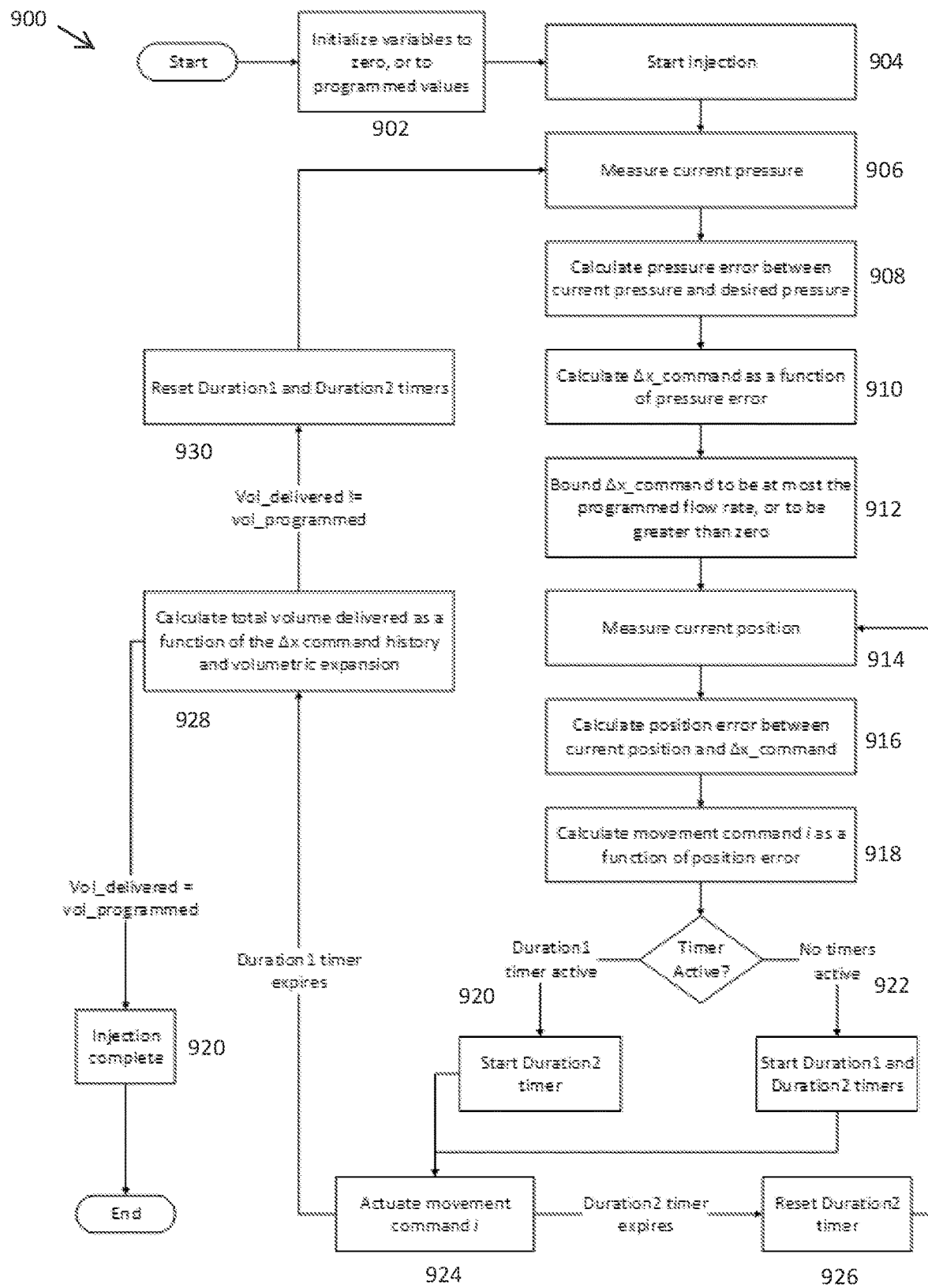
FIG. 16 is a representative flow chart of a flow control process in accordance with some non-limiting embodiments of the present disclosure.

Prior to initiating a fluid delivery procedure at step 904, such as via actuation of one or more drive components 510a, 510b, 510n of the fluid injector system 100 using the electronic control device 400, a programmed pressure for a specified time interval of the fluid delivery procedure and a maximum allowable change in pressure during any time interval are set to a predetermined value or initialized to zero at step 902 (see, also, P_set in FIG. 15). For example, the programmed pressure and the maximum allowable deviation or change in pressure may be stored in the memory 408 of the electronic control device 400.

At step 906, a first pressure is measured at the start of the time period and a second pressure is measured at the end of the time period. As described herein, pressure may be measured using one or more force sensors 540 associated with the one or more drive components 510a, 510b, 510n and/or one or more pressure sensors 550 associated with one or more of fluid reservoirs 500a, 500b, 500n and/or the fluid conduit 530.

At step 908, an error in pressure is determined. The error in pressure may be a difference between the measured pressure and a programmed or desired pressure.

At step 910, a change in the commanded position of the one or more drive components 510a, 510b, 510n is calculated as a function of pressure error determined in step 908 using Equation 1 (see, also, Δx_command in FIG. 15). A proportional-integral-derivative controller can be used for this determination as a function of the pressure error (see PID1 in FIG. 15). Tau (τ) is the small amount of time it takes to transfer or convert the pressure data to be usable by the processor for further action. For example, according to an embodiment, if a pressure is taken at time t=t1, the processor won't receive the data (due to hardware or software delays, filtering, etc.) until time t=t1+τ1, where τ1 is .the delay between transfer/conversion delay for the first measurement. According to various embodiments, tau (τ) is very small (microseconds) but may have a material effect on the value of the PID gains when the gains are tuned for a particular system. Referring to FIG. 15, Timer1 corresponds to the outer pressure PID loop in the updated FIG. 15; timer2 corresponds to the inner position PID loop. According to various embodiments, the calculated motor command, i is applied to the motor for the duration of timer2. When timer2 expires, drive component position is measured 914 (below) and position error is calculated 916, and a new motor command i is calculated 918. The motor command loop is repeated N times with timer2 until timer1 expires, at which point pressure is re-measured, pressure error is calculated, and the PID loop starts again with a new delta x_command.

At step 912, upper and lower limits of the change in the commanded position are set to be greater than zero and less than the programmed or desired flow rate.

At step 914, a current position of the one or more drive components 510a, 510b, 510n is determined. In some embodiments, the position of the one or more drive components 510a, 510b, 510n may be determined using information from an encoder or a stepper motor.

At step 916, an error in position of the one or more drive components 510a, 510b, 510n is determined (see, e.g., x_measured in FIG. 15). In some embodiments, the error is position of the one or more drive components 510a, 510b, 510n may be a difference between the current position of the one or more drive components 510a, 510b, 510n and the commanded position of the one or more drive components 510a, 510b, 510n.

At step 918, a movement command for the one or more drive components 510a, 510b, 510n is determined as a function of the position error determined in step 916. The movement command may be expressed using Equation 2. A second proportional-integral-derivative controller may be used for this determination (see PID2 in FIG. 15). As with tau1, tau2 (τ2) is the small delay between the measurement at t2 and the transfer/conversion delay for t2 to reach the processor.

At step 920, if no timers are active, a first timer and a second timer are started. The first timer is equal to the duration of a number of iterations of the pressure control loop based on the first timer, which is set to a predetermined length of time.

At step 922, if the first timer is active, the second timer is started. The movement command for the one or more drive components 510a, 510b, 510n is actuated in step 924 following start of first and second timers (step 920), or start of the second timer (step 922).

At step 926, if the second timer expires during movement of the one or more drive components 510a, 510b, 510n, the second timer is reset, and steps 914-924 are repeated.

If the first timer expires during movement of the one or more drive components 510a, 510b, 510n, the total volume of fluid that has been delivered is calculated at step 928 as a function of the change in position of the one or more drive components 510a, 510b, 510n and any volumetric expansion, such as due to capacitance of the system.

If the total volume of fluid delivered is not equal to the programmed or desired volume of fluid, the first and second timers are reset at step 930, and steps 906-924 are repeated.

If the total volume of fluid that has been delivered is equal to the programmed or desired volume of fluid, the fluid delivery procedure is terminated at step 932.

Figure 14A:
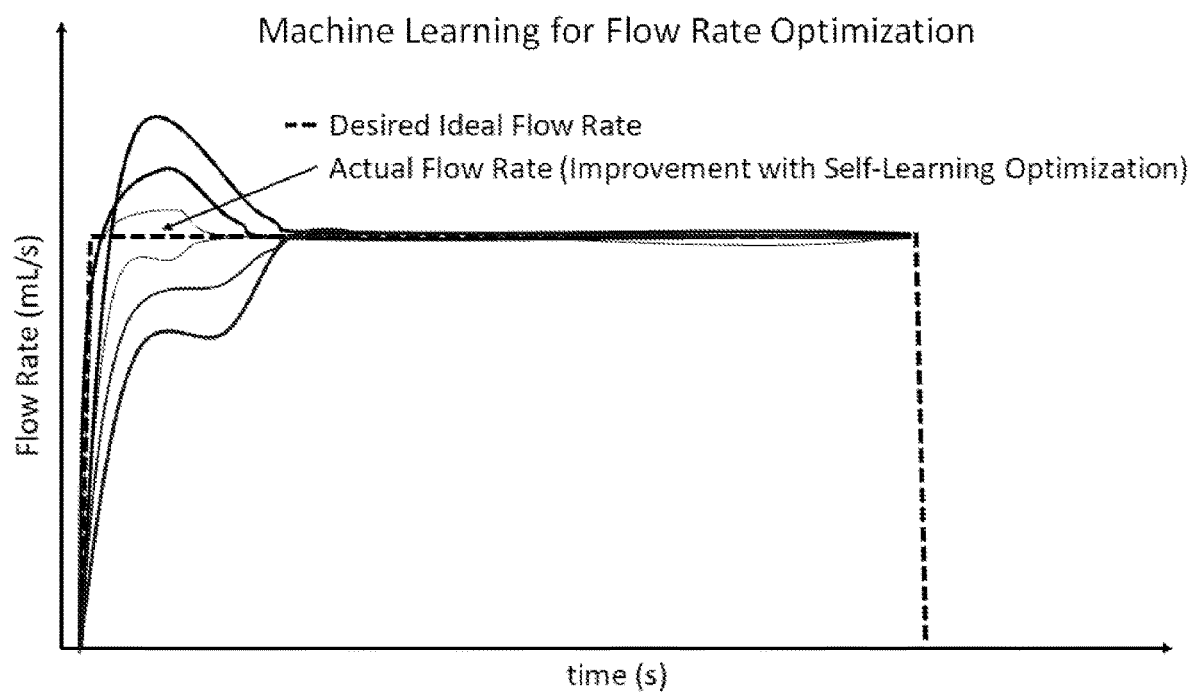
FIG. 14A is a graph of a plurality of pressure curves as a function of time used in machine learning for pressure optimization in accordance with some non-limiting embodiments of the present disclosure.
Figure 14B:
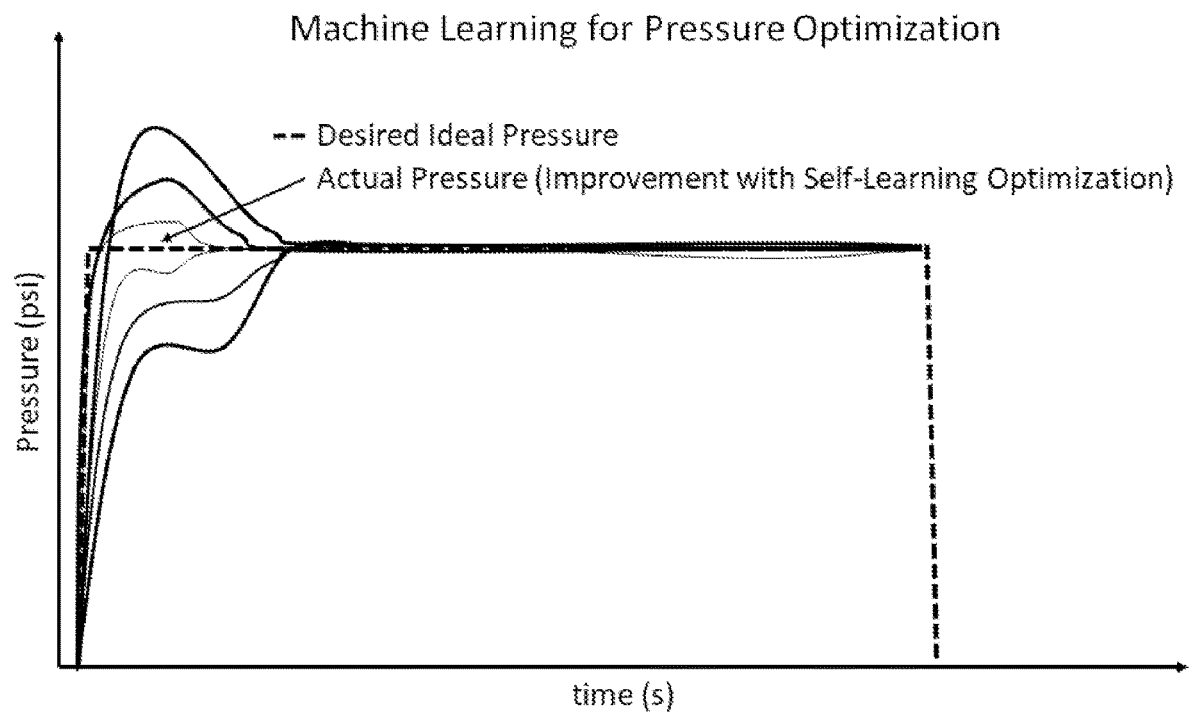
FIG. 14B is a graph of a plurality of flow rate curves as a function of time used in machine learning for flow rate optimization in accordance with some non-limiting embodiments of the present disclosure.

In some non-limiting embodiments, fluid delivery using real-time, pressure-based control of one or more drive components 510a, 510b, 510n of a fluid injector system 100 during a fluid injection procedure may be applied to a machine learning model based on a training dataset. For example, the fluid injector system 100, such as the control device 400 of the fluid injector system 100, may generate the machine learning model based on the training dataset to provide an improved fluid delivery output based on a desired fluid volume and delivery rate. Pressure and flow rate optimization curves that may be used as training data are shown in FIGS. 14A-14B.

In some non-limiting embodiments, the machine learning model may be designed to receive, as an input, data associated with an injection procedure, such as a desired flow rate during execution of a fluid delivery procedure, and provide, as an output, instructions to the control device 400 to drive the one or more drive components 510a, 510b, 510n to deliver a desired volume of fluid at a desired flow rate. In some non-limiting embodiments, the fluid injector system 100 may store the machine learning model (e.g., for later use) in the memory of the control device 400.

In some non-limiting embodiments, as described herein, the control device 400 of the fluid injector system 100 may process data associated with fluid delivery procedures conducted during a time interval (e.g., historical data associated with previous fluid delivery procedures) to obtain training data (e.g., a training dataset) for the machine learning model. For example, the control device 400 may process the data to change the data into a format that may be analyzed to generate the machine learning model. The data that is changed (e.g., the data that results from the change) may be referred to as training data. In some non-limiting embodiments, the control device 400 may process the data associated with previous fluid delivery procedures conducted during a selected time interval to obtain the training data based on receiving the data.

In some non-limiting embodiments, the control device 400 may analyze the training data to generate the machine learning model. For example, the control device 400 may use machine learning techniques to analyze the training data to generate the machine learning model. In some non-limiting embodiments, generating the machine learning model (e.g., based on training data obtained from historical data associated with previous fluid delivery procedures conducted during a selected time interval) may be referred to as training the machine learning model. The machine learning techniques may include, for example, supervised and/or unsupervised techniques, such as decision trees, random forests, logistic regressions, linear regression, gradient boosting, support-vector machines, extra-trees (e.g., an extension of random forests), Bayesian statistics, learning automata, Hidden Markov Modeling, linear classifiers, quadratic classifiers, association rule learning, and/or the like. In some non-limiting embodiments, the machine learning model may include a model that is specific to a particular characteristic, for example, a model that is specific to a particular fluid injector system 100, a particular user of the fluid injector system 100, a particular group of fluid injector systems 100 associated with a particular health institution, and/or the like. Additionally or alternatively, the machine learning model may be specific to a particular entity (e.g., a health care entity, such as a hospital). In some non-limiting embodiments, the control device 400 may generate one or more machine learning models for one or more entities, a particular group of entities, and/or one or more users of one or more entities.

Additionally or alternatively, when analyzing the training data, the control device 400 may identify one or more variables (e.g., one or more independent variables) as predictor variables (e.g., features) that may be used to make a prediction when analyzing the training data. In some non-limiting embodiments, values of the predictor variables may be inputs to the machine learning model. For example, the control device 400 may identify a subset (e.g., a proper subset) of the variables as the predictor variables that may be used to accurately predict the parameters for a fluid delivery procedure.

In some non-limiting embodiments, control device 400 may validate the machine learning model. For example, control device 400 may validate the machine learning model after control device 400 generates the machine learning model. In some non-limiting embodiments, control device 400 may validate the machine learning model based on a portion of the training data to be used for validation. For example, control device 400 may partition the training data into a first portion and a second portion, where the first portion may be used to generate the machine learning model, as described above. In this example, the second portion of the training data (e.g., validation data) may be used to validate the machine learning model.

In some non-limiting embodiments, the control device 400 may validate the machine learning model by providing validation data associated with the fluid injector system 100, such as instructions to the control device 400 to drive the one or more drive components 510a, 510b, 510n to deliver a desired volume of fluid at a desired flow rate, as input to the machine learning model, and determining, based on an output of the machine learning model, such as the volume of fluid delivered and a flow rate at which the volume is delivered, whether the machine learning model correctly, or incorrectly, predicted the fluid injection parameters required to meet the requested volume and flow rate. In some non-limiting embodiments, the control device 400 may validate the machine learning model based on a validation threshold. For example, the control device 400 may be configured to validate the machine learning model when the volume and flow rate are correctly predicted by the machine learning model (e.g., when the machine learning model correctly predicts a predefined percentage (such as, for example, more than 70%) of instructions to drive the one or more drive components 510a, 510b, 510n to deliver a desired volume of fluid at a desired flow rate).

In some non-limiting embodiments, if the control device 400 does not validate the machine learning model (e.g., when a percentage of correctly predicted fluid injection procedures does not satisfy the validation threshold), then the control device 400 may generate one or more additional machine learning models.

In some non-limiting embodiments, once the machine learning model has been validated, the control device 400 may further train the machine learning model and/or generate new machine learning models based on receiving new training data. The new training data may include additional data associated with one or more fluid delivery procedures. The control device 400 may use the machine learning model to predict fluid injection parameters and compare an output of machine learning models to the new training data that includes data associated with additional fluid injection procedures. In such an example, the control device 400 may update one or more machine learning models based on the new training data.

Although the disclosure has been described in detail for the purpose of illustration based on what are currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment.

The invention claimed is:

1. A fluid injector system configured for use in administering at least one fluid to a patient, the fluid injector system comprising:
a memory for storing therein a programmed flow rate to be delivered during execution of a fluid delivery procedure using a fluid injector and a maximum allowable deviation in the programmed flow rate;
at least one sensor configured for measuring a pressure of the at least one fluid, wherein the pressure is generated by at least one drive component of the fluid injector during execution of the fluid delivery procedure; and
a control device operatively associated with the at least one drive component of the fluid injector, the control device including at least one processor programmed or configured to perform an operation comprising:
determining an actual flow rate during a specified time interval of the fluid delivery procedure based on a change in pressure measured by the at least one sensor over the specified time interval;
determining a deviation of the actual flow rate from the programmed flow rate over the specified time interval; and
calculating a new programmed flow rate for a subsequent time interval after the specified time interval based on the programmed flow rate and the deviation of the actual flow rate from the programmed flow rate over the specified time interval.

2. The fluid injector system of claim 1, wherein the control device including the at least one processor is further programmed or configured to perform an operation comprising comparing the maximum allowable deviation to the deviation of the actual flow rate from the programmed flow rate over the specified time interval to determine a flow rate correction, and calculating the new programmed flow rate for the subsequent time interval based on the programmed flow rate and the flow rate correction.

3. The fluid injector system of claim 2, wherein the flow rate correction is equal to the maximum allowable deviation if the determined deviation of the actual flow rate from the programmed flow rate is greater than the maximum allowable deviation.

4. The fluid injector system of claim 3, wherein a difference between the deviation of the actual flow rate from the programmed flow rate and the maximum allowable deviation is stored as a buffer deviation for use in determining a new flow rate correction in one or more subsequent time intervals after the second time interval.

5. The fluid injector system of claim 2, wherein the flow rate correction is equal to the actual flow rate if the deviation of the actual flow rate from the programmed flow rate is less than or equal to the maximum allowable deviation.

6. The fluid injector system of claim 2, wherein the control device is configured to use a machine learning model designed to receive, as an input, data associated with the fluid injection procedure, and provide, as an output, instructions to drive the one or more drive components to deliver a desired volume of fluid at the programmed flow rate.

7. The fluid injector system of claim 1, wherein the operation to determine the actual flow rate during the specified time interval comprises measuring a first pressure using the at least one sensor at a beginning of the specified time interval and measuring a second pressure using the at least one sensor at an end of the specified time interval and converting the first pressure and the second pressure to a change in pressure corresponding to the actual flow rate during the specified time interval.

8. The fluid injector system of claim 7, wherein the change in pressure is based on a difference between the second pressure and the first pressure, and at least one scaling factor that is determined by one or more features of the fluid injector.

9. The fluid injector system of claim 2, wherein the flow rate correction for each subsequent time interval is based on a difference between the maximum allowable deviation and the deviation of the actual flow rate from the new programmed flow rate over each subsequent time interval, and a buffer deviation from at least one previous time interval.

10. The fluid injector system of claim 1, wherein the operation performed by the control device further comprises the operation to repeat the steps of the operation for each subsequent time interval in the fluid injection procedure, wherein the new programmed flow rate is used as the programmed flow rate.

11. The fluid injector system of claim 1, wherein the operation performed by the control device further comprises delivering the fluid at the new programmed flow rate in the subsequent time interval.

12. A computer-implemented method for monitoring performance of a fluid injector system configured for use in administering at least one fluid to a patient, the method comprising:
storing, in a memory device, a programmed flow rate for the fluid to be delivered and a maximum allowable deviation in the programmed flow rate during a fluid delivery procedure using a fluid injector;
measuring, using at least one sensor, a pressure of the at least one fluid generated by at least one drive component of the fluid injector during execution of the fluid delivery procedure;
determining, with a control device comprising at least one processor, an actual flow rate during a specified time interval of the fluid delivery procedure based on a change in pressure measured by the at least one sensor over the specified time interval;
determining, with the control device, a deviation of the actual flow rate from the programmed flow rate over the specified time interval; and
calculating, with the control device, a new programmed flow rate for a subsequent time interval after the specified time interval based on the programmed flow rate and the deviation of the actual flow rate from the programmed flow rate over the specified time interval.

13. The computer-implemented method of claim 12, further comprising comparing, with the control device, the maximum allowable deviation to the deviation of the actual flow rate from the programmed flow rate over the specified time interval to determine a flow rate correction, and calculating the new programmed flow rate for the subsequent time interval based on the programmed flow rate and the flow rate correction.

14. The computer-implemented method of claim 13, wherein the flow rate correction is equal to the maximum allowable deviation if the determined deviation of the actual flow rate from the programmed flow rate is greater than the maximum allowable deviation.

15. The computer-implemented method of claim 14, wherein a difference between the deviation of the actual flow rate from the programmed flow rate and the maximum allowable deviation is stored as a buffer deviation for use in determining a new flow rate correction in one or more subsequent time intervals after the second time interval.

16. The computer-implemented method of claim 13, wherein the flow rate correction is equal to the actual flow rate if the deviation of the actual flow rate from the programmed flow rate is less than or equal to the maximum allowable deviation.

17. The computer-implemented method of claim 13, wherein the control device is configured to use a machine learning model designed to receive, as an input, data associated with the fluid injection procedure, and provide, as an output, instructions to drive the one or more drive components to deliver a desired volume of fluid at the programmed flow rate.

18. The computer-implemented method of claim 12, wherein determining the actual flow rate during the specified time interval comprises measuring a first pressure using the at least one sensor at a beginning of the specified time interval and measuring a second pressure using the at least one sensor at an end of the specified time interval and converting the first pressure and the second pressure to a change in pressure corresponding to the actual flow rate during the specified time interval.

19. The computer-implemented method of claim 18, wherein the change in pressure is based on a difference between the second pressure and the first pressure, and at least one scaling factor that is determined by one or more features of the fluid injector.

20. The computer-implemented method of claim 13, wherein the flow rate correction for each subsequent time interval is based on a difference between the maximum allowable deviation and the deviation of the actual flow rate from the new programmed flow rate over each subsequent time interval, and a buffer deviation from at least one previous time interval.

21. The computer-implemented method of claim 12, further comprising repeating the determining and calculating steps for each subsequent time interval in the fluid injection procedure, wherein the new programmed flow rate is used as the programmed flow rate.

22. The computer-implemented method of claim 12, further comprising delivering the fluid at the new programmed flow rate in the subsequent time interval.

* * * * *

UNITED STATES PATENT AND TRADEMARK OFFICE
CERTIFICATE OF CORRECTION

PATENT NO. : 12,070,577 B2
APPLICATION NO. : 17/776332
DATED : August 27, 2024
INVENTOR(S) : McDermott et al.

Page 1 of 1

It is certified that error appears in the above-identified patent and that said Letters Patent is hereby corrected as shown below:

In the Specification

In Column 13, Line 26, delete "and [[in]] which" and insert -- and which --, therefor.
In Column 23, Line 52, delete "(ΔPs=Δ*ΔP+B," and insert -- (ΔPs=A*ΔP+B, --, therefor.

Signed and Sealed this
Eleventh Day of February, 2025

Coke Morgan Stewart
*Acting Director of the United States Patent and Trademark Office*